(12) United States Patent
Yokoi et al.

(10) Patent No.: US 6,884,419 B1
(45) Date of Patent: Apr. 26, 2005

(54) HG-CSF FUSION POLYPEPTIDE HAVING C-MPL ACTIVITY, DNA CODING FOR SAME AND METHODS OF TREATING ANEMIA USING SAME

(75) Inventors: Haruhiko Yokoi, Ibaraki (JP); Yukimasa Shiotsu, Tokyo (JP); Noboru Konishi, Yamaguchi (JP); Hideharu Anazawa, Tokyo (JP); Tatsuya Tamaoki, Tokyo (JP); Motoo Yamasaki, Tokyo (JP); Yoko Kato, Tokyo (JP); Kazuhisa Uchida, Tokyo (JP); Kinya Yamashita, Shizuoka (JP)

(73) Assignee: Kyowa Hakko Kogyo, Co., Ltd., Tokyo (JP)

( * ) Notice: Subject to any disclaimer, the term of this patent is extended or adjusted under 35 U.S.C. 154(b) by 201 days.

(21) Appl. No.: 09/680,514

(22) Filed: Oct. 6, 2000

Related U.S. Application Data

(63) Continuation-in-part of application No. 08/765,337, filed on Dec. 23, 1996, now abandoned.

(51) Int. Cl.$^7$ ............................................... A61K 38/19
(52) U.S. Cl. ................ 424/192.1; 424/85.1; 424/198.1; 435/69.7; 435/69.5; 530/351
(58) Field of Search .............................. 424/85.1, 85.2, 424/192.1, 198.1; 530/351; 514/2, 8, 12; 435/69.5, 71.2, 172.3, 325, 252.3, 320, 69.7; 536/23.1, 23.4, 23.5

(56) References Cited

U.S. PATENT DOCUMENTS

| | | | |
|---|---|---|---|
| 4,999,291 A | * | 3/1991 | Souza |
| 5,073,627 A | * | 12/1991 | Curtis et al. |
| 5,641,655 A |   | 6/1997 | Foster et al. |
| 5,989,537 A | * | 11/1999 | Holly et al. ................ 424/85.1 |

FOREIGN PATENT DOCUMENTS

| | | | |
|---|---|---|---|
| EP | 0335423 B1 | | 3/1989 |
| EP | 0 335 423 B1 | * | 10/1989 |
| EP | 0544292 A2 | | 11/1992 |
| JP | A-4-103599 | | 4/1992 |
| WO | WO 90/12877 | | 11/1990 |
| WO | WO92/04455 | | 3/1992 |

OTHER PUBLICATIONS

"Cytokines", A. Mire–Sluis et al., ed., Academic Press, San Diego, 1998. pp. 237–238, 330–331.*
Janis Kuby, "Immunology", W.H. Freeman and Company, NY, 1992, pp. 42 and 44.*
Frederick J. de Sauvage et al "Stimulation of Megakaryocytopoiesis and Thrombopoiesis by the C–MPL Ligand" Nature (1994) vol. 369, pp 533–538.
Callard et al The Cytokine Facts Book 1994 pp 46 etc.
Paul et al Proc. Natl. Acad. Sci. vol. 87 pp 7512–7516 10/90 Genetics Molecular Cloning of a cDNA encoding interleukin 11, a stromal cell–derived lymphopoietic and hematopoietic cytoking.
Rock et al Protein Engineering vol. 5 No. 6 pp 584–591, 1992, pp 583–591 Overexpression an structure—function analysis of a bioengineered II–21L–6 chimeric lymphokine.
Gillies et al Bioconjugate Chem. 1993, p 230–235 Biological Activity and in Vivo Clearance of Antitumor etc.
Feng et al Reports 9/88 pp 1501–1503 Antiproliferative Activity of a Hybrid Protein between Interferon–γ etc.
Mikayama et al Proc. Natl. Acad. Sci. USA vol. 90 pp 10056–10060.
Voet et al Biochemistry, John Wiley & Sons, Inc. pp 126–128 and 228–234.
Cuningham et al (1989) Science, vol. 244, pp 1081–1085.
George et al (1988) Molecular Sequencing & Synthesis chapter 12, pp 127–149 Alan R. Liss, Inc. New York.

* cited by examiner

*Primary Examiner*—Lorraine Spector
(74) *Attorney, Agent, or Firm*—Nixon & Vanderhye P.C.

(57) ABSTRACT

The present invention relates to a fusion polypeptide which comprises a polypeptide having G-CSF activity and a polypeptide having TPO activity and DNA which codes for the fusion polypeptide, to a fusion polypeptide in which a polypeptide having G-CSF activity and a polypeptide having TPO activity are fused via a spacer peptide and DNA which codes for the fusion polypeptide and to a polypeptide in which the fusion polypeptide comprising a polypeptide having G-CSF activity and a polypeptide having TPO activity is chemically modified with a polyalkylene glycol derivative. It also relates to an anemia-treating composition containing the fusion polypeptide as an active ingredient.

9 Claims, 3 Drawing Sheets

US 6,884,419 B1

HG-CSF FUSION POLYPEPTIDE HAVING C-MPL ACTIVITY, DNA CODING FOR SAME AND METHODS OF TREATING ANEMIA USING SAME

This is a continuation-in-part of application Ser. No. 08/765,337, filed Dec. 23, 1996, abandoned, which is a 371 U.S. national phase of PCT/JP96/01157, filed Apr. 25, 1996, which designated the U.S., the entire content of which is hereby incorporated by reference in this application.

TECHNICAL FIELD

The present invention relates to a fusion polypeptide comprising a polypeptide having a granulocyte colony stimulating factor (hereinafter referred to as "G-CSF") activity and a polypeptide having a platelet growth factor (thromboproietin, hereinafter referred to as "TPO") activity, and DNA which codes for the fusion polypeptide. Since the fusion polypeptide of the present invention can form and amplify platelets and neutrophils simultaneously, it is useful for the treatment of anemia and the like

BACKGROUND ART

Blood comprises hematopoietic cells such as erythrocytes, leukocytes, platelets and the like. These hematopoietic cells mature from only one kind of pluripotential blood stem cell through various differentiation steps. These steps undergo complex regulation by a group of proteinous factors which are generally referred to as cytokines. A certain type of cytokine takes part in the differentiation and multiplication of various hematopoietic cells. On the other hand, a certain type of hematopoietic cell undergoes regulation of its differentiation and multiplication by various types of cytokines. This is called overlapping cytokine actions. Among these cytokine members, TPO and G-CSF are considered to have small overlapping actions.

TPO mainly takes part in the formation of platelets. Platelets are formed by the fragmentation of megakaryocytes, a hematopoietic cell which has a large nucleus and is present mainly in bone marrow. Platelets are essential for forming blood clots at damaged portions in blood vessels. Platelets also play important roles in not only blood coagulation but also injury healing by releasing proteins having other functions at the damaged portions. A significant decrease in the number of platelets may be fatal, because the body may easily bleed.

G-CSF is a cytokine which accelerates activation of neutrophils, a member of the leukocytes, and differentiation of neutrophils from their precursor cells. Neutrophils exert the first defense action when invaded by foreign enemies such as bacteria, viruses and the like. When the number of neutrophils is decreased, the body becomes defenseless against infection, and this too is also often fatal.

Current medical treatment of cancers often cause side effects in which pluripotential blood stem cells are damaged by the administration of a chemotherapeutic drug, irradiation of X-rays or bone marrow transplantation for the treatment of leukemia, thus decreasing the number of all hematopoietic cells. Apparently, it is markedly beneficial for thrombopenia and leukopenia patients to amplify the number of these cells by the administration of cytokine, to suppress bleeding tendency and preventing infectious diseases.

A cytokine which can amplify platelets and neutrophils simultaneously has not been found, and there is no medicine having such an effect.

Leukemia inhibiting factors, stem cell factors, macrophage colony stimulating factors, granulocyte/macrophage colony stimulating factors, erythropoietin, interleukin (IL)-3, IL-6, IL-11, megakaryocyte colony stimulating factors and the like are known as substances which amplify platelets or enhance differentiation and multiplication of megakaryocytes [Metcalf et al., *Blood,* 80, 50–56 (1990); Hunt et al., *Blood,* 80, 904–911 (1992); Examined Japanese Patent Publication No. 6-11705; Hoffman et al., *Blood Cells,* 13, 75–86 (1987); Mazur et al., *Exp. Hematol.,* 15, 1123–1133 (1987); McNiece et al., *Exp. Hematol.,* 16, 807–810 (1988); Lu et al., *Brit. J. Hematol.,* 70; 149–156 (1988); Ishibashi et al., *Proc. Natl. Acad. Sci. USA,* 86, 5953–5957 (1989); WO 95/21919; WO 95/18858]. It is understood that these many cytokine members amplify platelets by overlapping actions. Recently, it was revealed that a receptor ligand called c-mpl is a cytokine which has the highest activity among platelet amplifying factors and acts directly [de Sauvage et al., *Nature,* 369, 533 (1994)].

As substances which multiply granulocytes, the above-mentioned IL-3, macrophage colony stimulating factors, granulocyte/macrophage colony stimulating factors and the like are known, but G-CSF has the highest activity in terms of multiplying neutrophils selectively [Nicola et al., *J. Biol. Chem.,* 258, 9017 (1983)]. With regard to a polypeptide in which two different kinds of cytokine are fused, there are reports in Japanese Published Unexamined International Patent Application No. 500116/94, U.S. Pat. No. 5,359,035, *Exp. Hematol.,* 21, 647–655 (1993) and ibid., 18, 615 (1990) and the like.

However, nothing is known about a fusion polypeptide in which TPO is used as one of the fused cytokines.

An object of the present invention is to provide a fusion polypeptide which can produce and amplify platelets and neutrophils simultaneously. This fusion polypeptide allows the formation of megakaryocyte colonies and neutrophil colonies and the differentiation or maturation of megakaryocyte precursor and neutrophil precursor can be controlled.

DISCLOSURE OF THE INVENTION

The present invention relates to a fusion polypeptide which comprises a polypeptide having G-CSF activity and a polypeptide having TPO activity and DNA which codes for the fusion polypeptide. Also disclosed are fusion polypeptides in which a polypeptide having G-CSF activity and a polypeptide having TPO activity are fused via a spacer peptide and DNA which codes for the fusion polypeptide; and a polypeptide in which the fusion polypeptide comprising a polypeptide having G-CSF activity and a polypeptide having TPO activity is chemically modified with a polyethylene glycol derivative. Also provided are anemia-treating compositions containing the fusion polypeptide as an active ingredient.

The fusion protein of the present invention has no mouse IL-3 activity.

As the polypeptide having G-CSF activity for use in the present invention, any protein may be used with the proviso that it has the requisite G-CSF activity, such as a polypeptide having the amino acid sequence shown in Table 1 [*Nature,* 319, 415 (1986)].

Also useful is a protein which has an amino acid sequence derived from the amino acid sequence shown in Table 1 (SEQ ID NOs:39 and 46) by substitution, deletion or addition of one or more amino acids, and examples thereof include hG-CSF derivatives shown in Table 2 and described in Japanese published Unexamined Patent Application No.

267299/88, Japanese Published Unexamined Patent application No. 299/88, and Japanese Published Unexamined International Patent Application No. 500636/88.

TABLE 1

```
X ThrProLeuGlyProAlaSerSerLeuProGlnSerPheLeuLeu
1               5              10              15
LysCysLeuGluGlnValArgLysIleGlnGlyAspGlyAlaAlaLeu
         20              25              30
GlnGluLysLeuCysAlaThrTyrLysLeuCysHisProGluGluLeu
     35              40              45
ValLeuLeuGlyHisSerLeuGlyIleProTrpAlaProLeuSerSer
  50              55              60
CysProSerGlnAlaLeuGlnLeuAlaGlyCysLeuSerGlnLeuHis
65              70              75
SerGlyLeuPheLeuTyrGlnGlyLeuLeuGlnAlaLeuGluGlyIle
80              85              90              95
SerProGluLeuGlyProThrLeuAspThrLeuGlnLeuAspValAla
           100             105             110
AspPheAlaThrThrIleTrpGlnGlnMetGluGluLeuGlyMetAla
       115             120             125
ProAlaLeuGlnProThrGlnGlyAlaMetProAlaPheAlaSerAla
     130             135             140
PheGlnArgArgAlaGlyGlyValLeuValAlaSerHisLeuGlnSer
   145             150             155
PheLeuGluValSerTyrArgValLeuArgHisLeuAlaGlnPro
160             165             170         174
```

(X represents H or Met.)

TABLE 2

| Position from N-terminal amino acid | Substituted amino acid in hG-CSF derivatives |||||||||||| |
|---|---|---|---|---|---|---|---|---|---|---|---|---|
| (hG-CSF in Table 1) | a) | b) | c) | d) | e) | f) | g) | h) | i) | j) | k) | l) |
| 1st (Thr) | * | Val | Cys | Tyr | Arg | * | Asn | Ile | Ser | * | Ala | * |
| 3rd (Leu) | Glu | Ile | Ile | Ile | Thr | Thr | Glu | Thr | Thr | * | Thr | * |
| 4th (Gly) | Lys | Arg | Arg | Arg | Arg | Arg | Arg | Arg | Arg | Arg | Tyr | * |
| 5th (Pro) | Ser | Ser | Ser | Ser | Ser | Ser | Ser | Ser | Ser | * | Arg | * |
| 17th (Cys) | Ser | Ser | Ser | Ser | Ser | Ser | Ser | Ser | Ser | Ser | Ser | Ser |

*unsubstituted amino acid

As the polypeptide having TPO activity for use in the present invention, any protein may be used with the proviso that it has the prerequisite TPO activity, such as the c-mpl ligand which is a peptide Having the amino acid sequence shown in table 3 [*Nature*, 369, 533 (1994)], as well as leukemia inhibiting factors, stem cell factors, macrophage colony stimulating factors, granulocyte/macrophage colony stimulating factors, erythropoietin, interleukin (IL)-3, IL-6, IL-11, megakaryocyte colony stimulating factors and the like.

TABLE 3

```
SerProAlaProProAlaCysAspLeuArgValLeuSerLysLeu
1               5              10              15
LeuArgAspSerHisValLeuHisSerArgLeuSerGlnCysPro
         20              25              30
GluValHisProLeuProThrProValLeuProAlaValAsp
       35              40              45
PheSerLeuGlyGluTrpLysThrGlnMetGluGluThrLysAla
           50              55              60
GlnAspIleLeuGlyAlaValThrLeuLeuLeuGluGlyValMet
         65              70              75
AlaAlaArgGlyGlnLeuGlyProThrCysLeuSerSerLeuLeu
           80              85              90
GlyGlnLeuSerGlyGlnValArgLeuLeuLeuGlyAlaLeuGln
         95             100             105
SerLeuLeuGlyThrGlnLeuProProGlnGlyArgThrThrAla
         110             115             120
HisLysAspProAsnAlaIlePheLeuSerPheGlnHisLeuLeu
       125             130             135
```

TABLE 3-continued

```
ArgGlyLysValArgPheLeuMetLeuValGlyGlySerThrLeu
           140             145             150
CysValArgArgAlaProProThrThrAlaValProSerArgThr
         155             160             165
SerLeuValLeuThrLeuAsnGluLeuProAsnArgThrSerGly
       170             175             180
LeuLeuGluThrAsnPheTHrAlaSerAlaArgThrThrGlySer
         185             190             195
GlyLeuLeuLysTrpGlnGlnGlyPheArgAlaLysIleProGly
         200             205             210
LeuLeuAsnGlnThrSerArgSerLeuAspGlnIleProGlyTyr
         215             220             225
LeuAsnArgIleHisGluLeuLeuAsnGlyThrArgGlyLeuPhe
         230             235             240
ProGlyProSerArgArgThrLeuGlyAlaProAspIleSerSer
         245             250             255
GlyThrSerAspThrGlySerLeuProProAsnLeuGlnProGly
         260             265             270
TyrSerProSerProThrHisProProThrGlyGlnTyrThrLeu
         275             280             285
PheProLeuProProThrLeuProThrProValValGlnLeuHis
         290             295             300
ProLeuLeuProAspProSerAlaProThrProThrProThrSer
         305             310             315
ProLeuLeuAsnThrSerTyrThrHisSerGlnAsnLeuSerGln
         320             325             330
GluGly
332
```

The polypeptide having G-CSF activity and the other polypeptide having TPO activity, which constitute the fused polypeptide of the present invention, are not particularly limited, provided that they contain respective activity-producing portions. For example, when the c-mpl ligand is used as the polypeptide having TPO activity, it may contain an amino acid sequence of the 153rd and 154th positions counting from the N-terminal amino acid.

Also included in the polypeptide of the present invention is a polypeptide in which a polypeptide having G-CSF activity and a polypeptide having TPO activity are fused via a spacer peptide. As the spacer peptide, any sequence may be used with the proviso that it does not spoil the G-CSF activity and TPO activity. For example, the peptide shown in Table 4 can be used as the spacer peptide.

TABLE 4

| Linker |
|---|
| (GlyGlyGlySer)$_3$Arg |
| (SerGlyGlyGly)$_4$Arg |
| SerGlyGlyGlyArg |
| (SerGlyGlyGly)$_4$ |
| SerGlyGlyGly |
| (GlyGlyGlySer)$_3$ |
| (GlyGlyGlySer)$_2$ |

Examples of the fusion polypeptide of the present invention include a polypeptide having the amino acid sequence shown in Sequence ID No. 1, 2 or 3 and a polypeptide derived from the amino acid sequence of the fusion polypeptide by addition, deletion or substitution of one or more amino acids within such a range that the G-CSF activity and TPO activity are not spoiled, having a homology of 40% or more with the amino acid sequence of the polypeptide. The homology is preferably 60% or more, and more preferably 80% or more.

The substitution, deletion or addition of amino acids can be carried out in accordance with known methods described for example in *Nucleic Acid Research,* 10, 6487 (1982); *Proc. Natl. Acad. Sci., USA,* 79, 6409 (1982); *Proc. Natl. Acad. Sci., USA,* 81, 5662 (1984); *Science,* 224, 1431 (1984); PCT WO 85/00817; *Nature,* 316, 601 (1985); Gene, 34, 315 (1985);. *Nucleic Acid Research,* 13, 4431 (1985); and "Current Protocols in Molecular Biology", Chap. 8, Mutagenesis of Cloned DNA, John Wiley & Sons, Inc. (1989).

Also included in the fusion polypeptide of the present invention is a peptide having an amino acid sequence in which a secretion signal peptide is added to the N-terminal amino acid of the above-mentioned polypeptide; examples include a polypeptide having the amino acid sequence shown in Sequence ID Nos: 5, 7 or 9.

In addition, a fusion polypeptide having G-CSF activity and TPO activity, in which at least one amino group of the above-mentioned polypeptide is chemically modified with a polyalkylene glycol derivative, is also included in the fusion polypeptide of the present invention.

Examples of the polyalkylene derivative include a polyethylene glycol derivative, a polypropylene glycol derivative, a polyoxyethylene-polyoxypropylene copolymer derivative and the like. Polyethylene glycol-succinimidyl propionate is preferred.

The fusion polypeptide chemically modified with a polyethylene glycol derivative can be prepared in accordance with the method described in Japanese Examined Patent Publication No. 96558/95.

The DNA which codes for the fusion polypeptide (hereinafter referred to as "TPO-CSF") of the present invention can be obtained by polymerase chain reaction (PCR) and the like based on the known nucleotide sequences of a polypeptide having TPO activity and a polypeptide having G-CSF activity. It can also be obtained by chemical synthesis.

Examples of DNA which codes for TPO-CSF include a DNA containing a nucleotide sequence that codes for a polypeptide having the amino acid sequence shown in Sequence ID No. 1, 2 or 3 or a polypeptide derived from the amino acid sequence of the polypeptide by substitution, deletion or addition of one or more amino acids but having the G-CSF activity and TPO activity, such as a DNA which contains the nucleotide sequence shown in Sequence ID Nos: 4, 6 or 8.

Other examples are DNA's in which mutation such as substitution mutation, deletion mutation, insertion mutation or the like is introduced into the above-mentioned DNA within such a range that the G-CSF activity and TPO activity are not spoiled, which can be obtained, for example, by colony hybridization or plaque hybridization using a DNA containing. the nucleotide sequence shown in Sequence ID Nos: 4, 6 or 8 as a probe.

An example is a DNA which is identified by carrying out hybridization of a membrane filter on which colony- or plaque-originated DNA is fixed, at 65° C. in the presence of 0.7 to 1.0 M sodium chloride using a DNA containing the nucleotide sequence shown in Sequence ID Nos: 4, 6 or 8 as a probe, and subsequently washing the resulting filter at 65° C. in 0.1 to 2-fold SSC solution (1-fold SSC contains 150 mM sodium chloride and 15 mM sodium citrate).

The hybridization techniques are described in "Molecular Cloning, A laboratory manual", second edition (edited by Sambrook, Fritsch and Maniatis, Cold Spring Harbor Laboratory Press, 1989).

All polypeptides encoded by the DNA defined in the foregoing are included in the TPO-CSF.

Examples of plasmids containing the TPO-CSF-encoding DNA include pBS-T153LND28, pBS-T154ND28 and pBS-T153ND28LN1. *Escherichia coli* TLN-1 as a colon *bacillus* containing pBS-T153LND28 and *Escherichia coli* TN-1 as a colon *bacillus* containing pBS-T154ND28 have been deposited on Feb. 16, 1995, in National Institute of Bioscience and Human-Technology, Agency of Industrial Science and Technology, Higashi 1-1-3, Tsukuba-shi, Ibaraki, Japan (the postal code: 305), and have been assigned the designations as FERM BP-5001 and FERM BP-5002, respectively.

In order to express the thus obtained TPO-CSF-encoding gene (hereinafter referred to as "TPO-CSF gene") in a host, a DNA fragment containing the TPO-CSF gene is first cleaved into a TPO-CSF gene-containing DNA of an appropriate length with restriction enzymes or DNA hydrolyzing enzymes and inserted into downstream site of a promoter gene on an expression vector and then the thus DNA-inserted expression vector is introduced into a host suitable for the expression vector.

As the host, any host capable of expressing the intended gene can be used. Examples thereof include microbial strains belonging to the genera *Escherichia, Serratia, Corynebacterium, Brevibacterium, Pseudomonas, Bacillus* and the like, as well as yeast strains, animal cell hosts and the like.

Useful as the expression vector is a vector which can replicate by itself in the above-mentioned host or can be inserted into its chromosome and has a promoter at a site where transcription of the TPO-CSF gene can be made.

When a microorganism such as *Escherichia coli* or the like is used as the host, it is desirable that the TPO-CSF expression vector can replicate by itself in the microorganism and comprises a promoter, a ribosome binding sequence, the TPO-CSF gene and a transcription termination sequence. It may also contain a regulatory gene.

Examples of the expression vector include pBTrp2, pBTac1 and pBTac2 (all available from Boehringer-Mannheim Co.), pKYP10 (Japanese Published Unexamined Patent Application No. 110600/83), pKYP200 [*Agric. Biol. Chem.,* 48, 669 (1984)], pLSA1 [*Agric. Biol. Chem.,* 53, 277 (1989)], pGEL1 [*Proc. Natl. Acad. Sci., USA,* 82, 4306 (1985)], pBluescript (available from STRATAGENE Co.), pTrs30[ prepared from *Escherichia coli* JM109/pTrs30 (FERM BP-5407)], pTrs32 [prepared from *Escherichia coli* JM109/pTrs32 (FERM BP-5408)], pAGE107 [Japanese Published Unexamined Patent Application No. 22979/91; Miyaji et al., *Cytotechnology,* 3, 133 (1990)], pAS3-3 (Japanese Published Unexamined Patent Application No. 227075/90) and pAMoERC3Sc CDM8 [Brian Seed et al., *Nature,* 329, 840 (1987)].

As the promoter, any one capable of exerting expression in a host such as *Escherichia coli* or the like can be used. Examples thereof include promoters originated from

*Escherichia coli*, phages and the like, such as trp promoter (Ptrp)*, lac promoter (Plac), PL promoter, $P_R$ promoter and the like. Also useful are artificially designed and modified promoters such as a promoter prepared by connecting two Ptrp promoters in series (Ptrpx 2), tac promoter and the like.

As the ribosome binding sequence, any sequence capable of exerting expression in a host such as *Escherichia coli* or the like can be used, but it is desirable to use a plasmid in which the ribosome binding sequence and the initiation codon are arranged with an appropriate distance (for example, 6 to 18 bases).

Any gene which codes for TPO-CSF can be used as the TPO-CSF gene, but it is desirable to use the gene by substituting its bases in such a manner that the DNA sequence of the gene has codons most suitable for its expression in host microorganisms.

Although the transcription termination sequence is not always necessary for the expression of the gene, it is desirable to arrange the transcription termination sequence preferably just downstream of the structural gene.

Examples of the host include *Escherichia coli* XL1-Blue, *Escherichia coli* XL2-Blue, *Escherichia coli* DH1, *Escherichia coli* DH5 α, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Bacillus subtilis*, *Bacillus amyloliquefacience*, *Brevibacterium immariophilum* ATCC 14068, *Brevibacterium saccharolyticum* ATCC 14066, *Brevibacterium flavum* ATCC 14067, *Brevibacterium lactofermentum* ATCC 13869, *Corynebacterium glutamicum* ATCC 13032, *Corynebacterium acetoacidophilum* ATCC 13870, *Microbacterium ammoniaphilum* ATCC 15354 and the like.

When a yeast strain is used as the host, YEp13 (ATCC 37115), YEp24 (ATCC 37051), YCp50 (ATCC 37419) or the like may be used as the expression vector.

Any type of promoter can be used, provided that it can exert expression in yeast strain hosts. Examples thereof include promoters of genes of hexose kinase and the like glycolytic pathway enzymes, gal 1 promoter, gal 10 promoter, heat shock protein promoter, MF α1 promoter, CUP 1 promoter and the like.

Examples of the host include *Saccharomyces cerevisiae*, *Schizosaccharomyces pombe*, *Kluyveromyces lactis*, *Trichosporon pullulans*, *Schwanniomyces alluvius* and the like.

When animal cells are used as the host, examples of useful expression vectors include pcDNA I/Amp, pcDNA I, pcDMB (all available from Funakoshi Co., Ltd.), pcDNA 3 (available from Invitrogen Co.), pAGE248, pAGE210 and the like.

Any promoter capable of exerting expression in the animal cell hosts can be used. For example, the promoter of human CMV IE (immediate early) gene may be used. Also, the enhancer of human CMV IE gene may be used together with the promoter.

Any gene which codes for TPO-CSF can be used as the TPO-CSF gene.

In general, only a portion of TPO-CSF expressed from the gene is secreted into the extracellular moiety, so that, in order to effect positive extracellular secretion of TPO-CSF from the host, it is desirable to prepare and use a gene having a sequence in which a nucleotide sequence coding for a signal peptide is added to the gene, in accordance with the method of Paulson et al. [C. Paulson et al., *J. Biol. Chem.*, 264, 17619 (1989)] and the method of Lowe et al. [John. B. Lowe et al., *Proc. Natl. Acad. Sci., USA*, 86, 8227 (1989); John. B. Lowe et al., *Genes Develop.*, 4, 1288 (1990)].

As the host, namalwa cells, HBT5637 (Japanese Published Unexamined Patent Application No. 299/88), COS cells, CHO cells and the like may be used.

Introduction of TPO-CSF gene-containing DNA into animal cells can be effected by any method, provided that it can introduce DNA into animal cells. For example, an electroporation method [Miyaji et al., *Cytotechnology*, 3, 133 (1990)], a calcium phosphate method (Japanese Published Unexamined Patent Application No. 227075/90), a lipofection method [Philip L. Felgner et al., *Proc. Natl. Acad. Sci., USA*, 84, 7413 (1987)] and the like may be used. Isolation and cultivation of a transformant can be effected in accordance with the method described in Japanese Published Unexamined Patent Application No. 227075/90 or Japanese Published Unexamined Patent Application No. 257891/90.

TPO-CSF can be produced by cultivating the thus obtained transformant in accordance with the usually used cultivating method.

When a transformant obtained by using *Escherichia coli*, yeast or the like microorganism as the host is cultivated, the medium may be either a natural medium or a synthetic medium, with the proviso that it contains carbon sources, nitrogen sources, inorganic salts and the like which can be assimilated by the microorganism and cultivating of the transformant can be made efficiently.

As the carbon sources, those which can be assimilated by respective microorganisms are used, which include carbohydrates such as glucose, fructose, sucrose, molasses containing them, starch, starch hydrolyzates and the like, organic acids such as acetic acid, propionic acid and the like and alcohols such as ethanol, propanol and the like.

Examples of useful nitrogen sources include ammonia, ammonium salts of various inorganic and organic acids, such as ammonium chloride, ammonium sulfate, ammonium acetate, ammonium phosphate and the like, and other nitrogen-containing compounds, as well as peptone, meat extract, yeast extract, corn steep liquor, casein hydrolyzate, soybean cake and soybean cake hydrolyzate, various fermented microbial cells and digests thereof.

Examples of useful inorganic materials include potassium dihydrogenphosphate, dipotassium hydrogenphosphate, magnesium phosphate, magnesium sulfate, sodium chloride, ferrous sulfate, manganese sulfate, copper sulfate, calcium carbonate and the like.

Cultivation is carried out under aerobic conditions by shaking, submerged-aerial stirring or the like. The temperature for the cultivation is preferably 15 to 40° C., and the period for the cultivation is generally 16 to 96 hours. The medium pH is controlled at 3.0 to 9.0 during the cultivation. Adjustment of the pH is carried out using an inorganic or organic acid, an alkaline solution, urea, calcium carbonate, ammonia and the like.

As occasion demands, antibiotics such as ampicillin, tetracycline and the like may be added to the medium during the cultivation.

When a microorganism transformed with an expression vector prepared using an inducible promoter is cultivated, an inducer may be added to the medium as occasion demands. For example, isopropyl-β-D-thiogalactopyranoside (IPTG) or the like may be added to the medium when a microorganism transformed with an expression vector prepared using lac promoter is cultivated, or indoleacetic acid (IAA) or the like when a microorganism transformed with an expression vector prepared using trp promoter is cultivated.

When a transformant obtained using animal cells as the host is cultivated, generally used RPMI 1640 medium, MEM medium (manufactured by Eagle Co. or GibcoBRL Co.), D-MEM medium (manufactured by GibcoBRL Co.) or any one of these media further supplemented with fetal bovine serum and the like may be used.

The cultivation is carried out, for example, in the presence of 5% $CO_2$. The temperature for the cultivation is preferably 35 to 37° C., and the period for the cultivation is generally 3 to 7 days.

As occasion demands, antibiotics such as kanamycin, penicillin and the like may be added to the medium during the cultivation.

Productivity can be increased using a gene amplification system in which dihydrofolate reductase gene and the like are used, in accordance with the method described in Japanese Published Unexamined Patent Application No. 227075/90.

The TPO-CSF of the present invention obtained in this manner can be purified by commonly used protein purification techniques.

For example, when the TPO-CSF is not secreted into outside moiety of the host cells, a culture broth of the transformant is subjected to centrifugation to collect cells in the culture broth, and the thus collected cells are washed and then disrupted using a sonicator, French press, Manton Gaulin homogenizer, Dynomil or the like, thereby obtaining a cell-free extract. Thereafter, the cell-free extract is subjected to centrifugation, and the TPO-CSF is purified from the resulting supernatant fluid making use of various techniques including salting out with ammonium sulfate or the like salt, anion exchange chromatography on diethylaminoethyl (DEAE)-Sepharose or the like, hydrophobic chromatography on Butylsepharose, Phenylsepharose or the like, molecular sieve-aided gel filtration and various types of electrophoresis such as isoelectric focusing and the like.

When the TPO-CSF is secreted, purified TPO-CSF can be obtained from a culture filtrate of the transformant in the same manner as the case of the above-mentioned treatment of cell-free extract supernatant.

When produced in *Escherichia coli* cells, it can be purified efficiently by the combination of the above-mentioned method with the method described in Japanese Published Unexamined Patent Application No. 267292/88.

Also, it is possible to produce the TPO-CSF of the present invention in the form of its fusion protein with another protein and to purify the product by affinity chromatography using a substance having affinity for the fused protein. For example, it is possible to produce the TPO-CSF of the present invention as its fusion protein with protein A and purify it by an immunoglobulin G-aided affinity chromatography, in accordance with the method of Lowe et al. [John. B. Lowe et al., *Proc. Natl. Acad. Sci., USA*, 86, 8227 (1989.); John. B. Lowe et al., *Genes Develop.*, 4, 1288 (1990)].

In addition, it can also be purified by affinity chromatography using antibodies specific for a polypeptide which has G-CSF activity, such as antibodies specific for G-CSF.

The TPO-CSF of the present invention can be used as it is or as pharmaceutical compositions in various dosage forms.

The pharmaceutical compositions of the present invention are produced by mixing an effective amount of TPO-CSF as the active ingredient uniformly with pharmacologically acceptable carriers.

Preferably, these pharmaceutical compositions may be prepared in the form of unit dose packages suitable for injection.

Injections for use in injection administration can be prepared by using a carrier such as distilled water, a salt solution of sodium chloride or of a mixture of sodium chloride with other inorganic salts, a sugar solution of mannitol, lactose, dextran, glucose or the like, an amino acid solution of glycine, arginine or the like, an organic acid solution, an organic base solution or a mixture solution comprising a salt solution and a sugar solution. In that case, the composition can be made into solutions, suspensions or dispersions in the usual way using auxiliaries which include an osmotic pressure adjusting agent, a plant oil such as sesame oil or soybean oil and a surface active agent such as lecithin or a nonionic surface active agent. These solutions can be made into solid preparations by powder making, freeze drying and the like means, which are dissolved again prior to their use.

The above-mentioned pharmaceutical compositions which contain the TPO-CSF of the present invention as the active ingredient are useful for the treatment anemia or patients who become anemic as a result of treatment of diseases.

BEST MODE OF CARRYING OUT THE INVENTION

EXAMPLE 1

Figure 1:
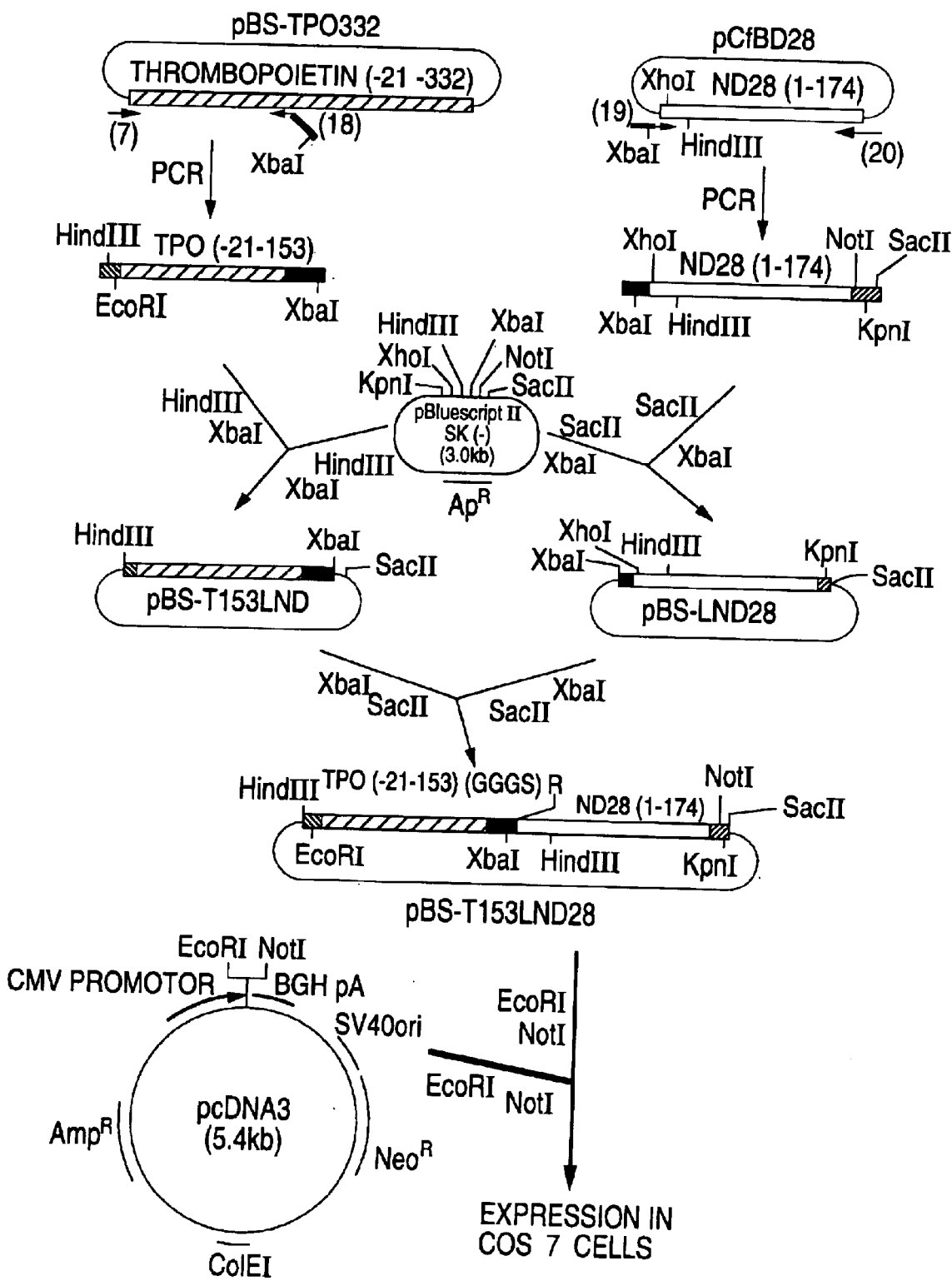
FIG. 1 is an illustration showing construction of a plasmid containing DNA which codes for TPO-ND28 (1).

Preparation of DNA which Codes for TPO-CSF

A DNA which codes for TPO-CSF was prepared in the following manner, using a DNA which codes for a polypeptide ND28 in which the 1st position amino acid residue of the amino acid sequence of human G-CSF was substituted by alanine (Ala), and the 3rd position amino acid by threonine (Thr), the 4th position amino acid by tyrosine (Tyr), the 5th position amino acid by arginine (Arg) and the 17th position amino acid by serine (Ser) (Japanese Published Unexamined Patent Application No. 267292/88) as a DNA which codes for a polypeptide having G-CSF activity, and a DNA that codes for a polypeptide having the amino acid sequence of Table 3 (de Sauvage et al., *Nature*, 369, 533 (1994); hereinafter referred to as "TPO") as a DNA which codes for a polypeptide having TPO activity. The fusion polypeptide of TPO and ND28 is abbreviated as TP0-ND28 hereinafter.

1. Preparation of TPO Gene

A TPO-encoding gene (hereinafter referred to as "TPO gene") for use in the preparation of TPO-ND28 was obtained by PCR in the following manner on the basis of the nucleotide sequence reported by de Sauvage et al. [*Nature*, 369, 533 (1994)].

A DNA shown in Sequence ID No. 7 containing 5' end nucleotide sequence of the TPO gene (hereinafter referred to as "primer 1") and a DNA shown in Sequence ID No. 8 containing 3' end nucleotide sequence of the TPO gene (hereinafter referred to as "primer 2") were synthesize using 380A DNA synthesizer of Applied Biosystems, Inc. In order to facilitate the cloning, a restriction enzyme recognition sequence was added to the terminus of each primer.

Amplification and cloning of the TPO gene translation region sequence were carried out by reverse transcription PCR using the primers 1 and 2, human liver poly A$^+$ mRNA (manufactured by Clontech Co., product No. CL 6510-1) mRNA and SuperScript Preamplification System for First Strand cDNA Synthesis Kit (manufactured by GibcoBRL Co.).

A 0.013 ml portion of aqueous solution containing 1,000 ng of human liver poly A$^+$ mRNA and 500 ng of oligo(dt) 12–18 (included in the kit) was treated at 70° C. for 10 minutes and then allowed to stand in ice for 1 minute.

The resulting solution was mixed with 0.002 ml of ten times-concentrated synthesis buffer, 0.001 ml of 10 mM dNTP mix, 0.002 ml of 0.1 M DTT and 0.001 ml of SuperScript II RT (200 kU/ml) (all included in the kit), and the mixture was allowed to stand at room temperature for 10 minutes and then incubated at 42° C. for 50 minutes. After completion of the incubation, the mixture was heated at 90° C. for 5 minutes to terminate the reverse transcription reaction.

The reaction solution was mixed with 0.001 ml of *E. coli* RNase H (2,000 U/ml; included in the kit) and incubated at 37° C. for 20 minutes.

A 0.1 ml portion of a reaction solution containing 0.005 ml of the above reaction solution, 400 nM of the primer 1, 400 nM of the primer 2, 20 mM of Tris-HCl (pH 8.2), 10 mM of potassium chloride, 0.01 mg/ml of bovine serum albumin (hereinafter referred to as "BSA"), 2 mM of magnesium chloride, 6 mM of ammonium sulfate, 0.1% Triton x-100, 10% dimethyl sulfoxide (hereinafter referred to as "DMSO"), 0.05 mM of deoxyadenosine triphosphate (hereinafter referred to as "dATP"), 0.05 mM of deoxycytidine triphosphate (hereinafter referred to as "dCTP"), 0.05 mM of deoxyguanosine triphosphate (hereinafter referred to as "dGTP") and 0.05 mM of deoxythymidine triphosphate (hereinafter referred to as "dTTP") was mixed with 2.5 units of Pfu polymerase (manufactured by Stratagene Co.) to carry out PCR using PERKIN ELMER CETUS DNA Thermal Cycler (manufactured by Takara Shuzo Co., Ltd.) by 35 time repetition of a three step incubation at 94° C. for 45 seconds, at 50° C. for 1 minute and at 72° C. for 2 minutes.

The resulting reaction solution was subjected to phenol/chloroform extraction and ethanol precipitation, and the thus obtained precipitate was dissolved in 0.015 ml of TE buffer [10 mM Tris-HCl (pH 8.0) and 1 mM ethylenediaminetetraacetic acid (hereinafter referred to as "EDTA")]

The thus prepared solution was mixed with restriction enzymes HindIII and KpnI to cleave the DNA amplified by PCR.

The resulting solution was subjected to an agarose gel electrophoresis, and a HindIII-KpnI treated DNA of about 1.1 kb was isolated from the agarose gel.

Using DNA Ligation Kit Ver. 1 (manufactured by Takara Shuzo Co., Ltd.), the thus isolated DNA (50 ng) was ligated with a HindIII-KpnI cleaved 2.9 kb fragment (30 ng) of a plasmid vector pBlueScript II SK(−) having a multicloning site (manufactured by Stratagene Co.) (volume of the reaction solution: 0.018 ml).

Using this reaction solution, an *Escherichia coli* strain DH5α (Library Efficiency DH5α Competent Cell, manufactured by GibcoBRL Co.) was transformed in the usual way, and the resulting transformant was spread on LB agar medium containing 50 µg/ml of ampicillin and cultivated overnight at 37° C.

Plasmids were isolated from several transformant strains grown on the medium in accordance with a known method [Birnboim et al., *Nucleic Acids Res.*, 7, 1513 (1979)].

Nucleotide sequence of the insertion fragment in each plasmid was determined using Taq DyeDeoxy Terminator Cycle Sequencing Kit (manufactured by Applied Biosystems Japan Inc., product No. 401113) and ABI373A DNA Sequencer (manufactured by Applied Biosystems Japan Inc.). In determining the nucleotide sequence, six DNA's having the nucleotide sequences of Sequence ID Nos. 9 to 13 or 14 and two primers having the nucleotide sequence shown in Sequence ID No. 15 or 16 containing a nucleotide sequence in the vector were synthesized based on the nucleotide sequence of TPO gene [de Sauvage et al., *Nature*, 369, 533 (1994)] and used as primers for the nucleotide sequence determination.

Determination of nucleotide sequence was carried out in accordance with the instructions attached to the kit and apparatus.

Of the above-mentioned plasmids, a plasmid pBS-TPO332 which coincided with the reported nucleotide sequence of the insertion fragment of TPO gene was used in the subsequent procedures.

2. Construction and Expression of DNA which Codes for TPO-ND28

Using the TPO-encoding DNA obtained in Example 1—1 and the ND28-encoding DNA obtained by the method described in Japanese Published Unexamined Patent Application No. 267292/88, a fusion polypeptide of TPO and ND28 (TPO on the N-terminal side and ND28 on the C-terminal side), TPO-ND-28, was prepared in the following manner.

1) Construction of DNA (Sequence ID No. 5) which Codes for TPO-ND28 (1) [Sequence ID No. 2; a Type Constructed Through a Linker (Gly Gly Gly Ser Gly Gly Gly Ser Gly Gly Gly Ser Arg; sequence ID No. 17)]

Though the mature type TPO comprises 332 amino acids, it is reported that its shortened protein consisting of its N-terminal side 153 amino acids can show the same activity of the complete length TPO [de Sauvage et al., *Nature*, 369, 533 (1994)], so that a DNA which codes for TPO-ND28 (1) in which the 153 amino acids from the N-terminal of TPO, used as its N-terminal side, was fused with the complete length ND28 (174 amino acids) as the C-terminal side through a linker (Gly Gly Gly Ser Gly Gly Gly Ser Gly Gly Gly Ser Arg) was prepared in the following manner (cf. FIG. 1).

(i) Preparation of DNA which Codes for the TPO Moiety of TPO-ND28 (1)

In order to prepare a DNA which codes for the TPO moiety of TPO-ND28 (1) by means of PCR, a DNA primer having a nucleotide sequence (Sequence ID No. 18) which corresponds to the linker was synthesized as the 3' end primer (hereinafter referred to as "primer 3").

Using the thus synthesized primer 3 and the primer 1 and pBS-TP0332, PCR was carried out in the following manner.

A 0.1 ml portion of a reaction solution containing 10 ng of pBS-TP0332, 400 nM of the primer 3, 400 nM of the primer 1, 20 mM of Tris-HCl (pH 8.2), 10 mM of potassium chloride, 0.01 mg/ml of BSA, 2 mM of magnesium chloride, 6 mM of ammonium sulfate, 0.1% Triton X-100, 10% DMSO, 0.05 mm of dATP, 0.05 mM of dCTP, 0.05 mM of dGTP and 0.05 mM of dTTP was mixed with 2.5 units of pfu polymerase to carry out PCR using PERKIN ELMER CETUS DNA Thermal Cycler (manufactured by Takara Shuzo Co., Ltd.) by 18 time repetition of a three step incubation at 94° C. for 45 seconds, at 50° C. for 1 minute and at 72° C. for 1 minute.

The resulting reaction solution was subjected to phenol/chloroform extraction and ethanol precipitation, and the thus obtained precipitate was dissolved in 0.015 ml of TE buffer.

The thus prepared solution was mixed with restriction enzymes HindIII and XbaI to cleave the DNA amplified by PCR.

The resulting solution was subjected to an agarose gel electrophoresis, and a HindIII-XbaI treated DNA fragment of about 0.6 kb was isolated from the agarose gel.

Using DNA Ligation Kit Ver. 1 (manufactured by Takara Shuzo Co., Ltd.), the thus isolated DNA fragment (100 ng) was ligated with a HindIII-XbaI cleaved 2.9 kb fragment (50 ng) of pBlueScript II SK(−) (volume of the reaction solution: 0.018 ml).

Using this reaction solution, the *Escherichia coli* strain DH5α was transformed in the usual way, and the resulting transformant was spread on LB agar medium containing 50 µg/ml of ampicillin and cultivated overnight at 37° C.

Plasmids were isolated from several transformant strains grown on the medium in accordance with a known method.

Nucleotide sequence of the insertion fragment in each plasmid was determined using Taq DyeDeoxy Terminator Cycle Sequencing Kit and ABI373A DNA Sequencer (manufactured by Applied Biosystems Japan Inc.). In determining the nucleotide sequence, primers having the nucleotide sequences of Sequence ID Nos. 9 to 12, 15 and 16 were used as primers for the nucleotide sequence determination.

Determination of nucleotide sequence was carried out in accordance with the instructions attached to the kit and apparatus.

Of the above-mentioned plasmids, plasmid pBS-T153LND which coincided with the reported nucleotide sequence of the insertion fragment of TPO gene was used in the subsequent procedures.

(ii) Preparation of DNA which Codes for the ND28 Moiety of TPO-ND28 (1)

In order to prepare a DNA which codes for the ND28 moiety of TPO-ND28 (1) by means of PCR, a primer having a nucleotide sequence (Sequence ID No. 19) which corresponds to the linker and the amino acid sequence of ND28 was synthesized as the 5' end primer (hereinafter referred to as "primer 4"), and a primer having a nucleotide sequence (Sequence ID No. 20) which corresponds to the C-terminal side amino acid sequence of ND28 was synthesized as the 3' end primer (hereinafter referred to as "primer 5").

Using the thus synthesized primers and plasmid pCfBD28 (Japanese Published Unexamined Patent Application No. 267292/88), PCR was carried out in the following manner.

A 0.1 ml portion of a reaction solution containing 10 ng of pCfBD28, 400 nm of the primer 4, 400 nM of the primer 5, 20 mM of Tris-HCl (pH 8.2), 10 mM of potassium chloride, 0.01 mg/ml of BSA, 2 mM of magnesium chloride, 6 mM of ammonium sulfate, 0.1% Triton X-100, 10% DMSO, 0.05 mM of DATP, 0.05 mM of dCTP, 0.05 mm of dGTP and 0.05 mM of dTTP was mixed with 2.5 units of Pfu polymerase to carry out PCR using PERKIN ELMER CETUS DNA Thermal Cycler (manufactured by Takara Shuzo Co., Ltd.) by 18 time repetition of a three step incubation at 94° C. for 45 seconds, at 50° C. for 1 minute and at 72° C. for 1 minute.

The resulting reaction solution was subjected to phenol/chloroform extraction and ethanol precipitation, and the thus obtained precipitate was dissolved in 0.015 ml of TE buffer.

The thus prepared solution was mixed with restriction enzymes SacII and XbaI to cleave the DNA amplified by PCR.

The resulting solution was subjected to an agarose gel electrophoresis, and a SacII-XbaI cleaved DNA fragment of about 0.5 kb was isolated from the agarose gel.

Using DNA Ligation Kit Ver. 1 (manufactured by Takara Shuzo Co., Ltd.), the thus isolated DNA fragment (100 ng) was ligated with a SacII-XbaI cleaved 2.9 kb fragment (50 ng) of pBlueScript II SK(−) (volume of the reaction solution: 0.018 ml).

Using this reaction solution, the *Escherichia coli* strain DH5α was transformed in the usual way, and the resulting transformant was spread on LB agar medium containing 50 µg/ml of ampicillin and cultivated overnight at 37° C.

Plasmids were isolated from several transformant strains grown on the medium in accordance with a known method.

Nucleotide sequence of the insertion fragment in each plasmid was determined using Taq DyeDeoxy Terminator Cycle Sequencing Kit and ABI373A DNA Sequencer. In determining the nucleotide sequence, two DNA's having the nucleotide sequence of Sequence ID No. 21 or 22 containing a nucleotide sequence of the ND28-encoding DNA and two DNA's having the nucleotide sequence of Sequence ID No. 15 or 16 containing a sequence present in the vector were used as primers for the nucleotide sequence determination.

Determination of nucleotide sequence was carried out in accordance with the instructions attached to the kit and apparatus.

Of the above-mentioned plasmids, plasmid pBS-LND28 in which the nucleotide sequence of the insertion fragment coincided with the nucleotide sequences of the ND28 gene and primers was used in the subsequent procedures.

(iii) Preparation of DNA which Codes for TPO-ND28 (1)

The DNA's respectively which code for the TPO moiety and ND28 moiety prepared in Example 1-2-1)-(i) and (ii) were fused in the following manner.

A 2,000 ng portion of pBS-T153LND was cleaved with restriction enzymes SacII and XbaI and subjected to an agarose gel electrophoresis to isolate a DNA fragment of about 3.5 kb.

Also, a 500 ng portion of pBS-LND28 was cleaved with restriction enzymes SacII and XbaI and subjected to an agarose gel electrophoresis to isolate a DNA fragment of about 0.5 kb.

Using DNA Ligation Kit Ver. 1 (manufactured by Takara Shuzo Co., Ltd.), the DNA fragment of about 3.5 kb (100 ng) was ligated with the DNA fragment of about 0.5 kb (100 ng) (volume of the reaction solution: 0.018 ml).

Using this reaction solution, the *Escherichia coli* strain DH5α was transformed in the usual way, and the resulting transformant was spread on LB agar medium containing 50 µg/ml of ampicillin and cultivated overnight at 37° C.

Plasmids were isolated from several transformant strains grown on the medium in accordance with a known method.

Structures of these plasmids were examined using restriction enzymes SacII and XbaI, and plasmid pBS-T153LND28 having a structure in which both of the DNA fragments are ligated with each other was used in the subsequent procedures.

2) Construction of DNA (Sequence ID No. 4) which codes for TPO-ND28 (2) [Sequence ID No. 1; a Type Constructed Without a Linker]

Figure 2:
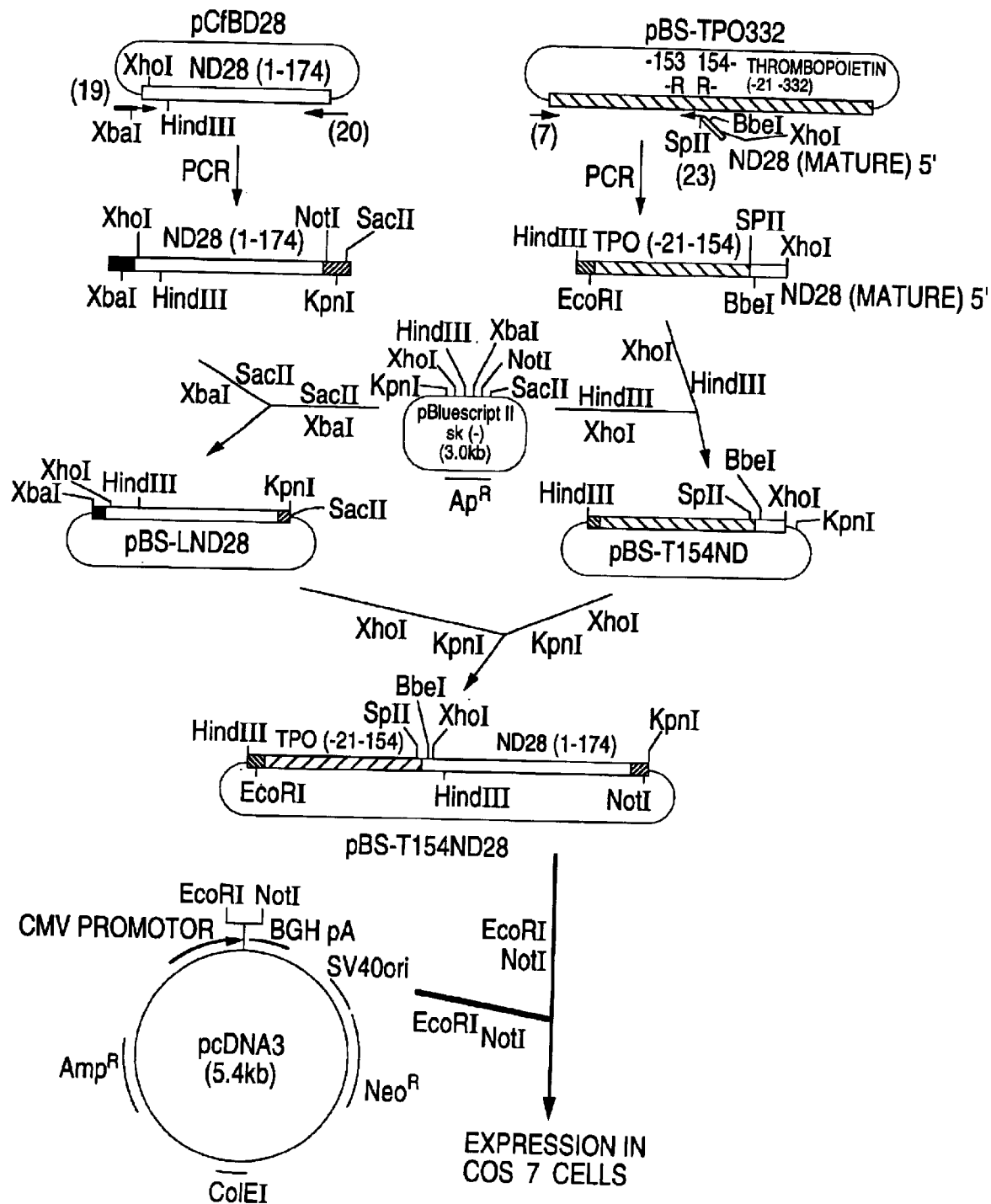
FIG. 2 is an illustration showing construction of a plasmid containing DNA which codes for TPO-ND28 (2).

A DNA which codes for TPO-ND28 (2) in which the 154 amino acids of TPO from its N-terminal were fused with the N-terminal of D28 (174 amino acids) was prepared in the following manner (cf. FIG. 2).

(i) Preparation of DNA which Codes for the TPO Moiety of TPO-ND28 (2)

In order to prepare a DNA which codes for the TPO moiety of TPO-ND28 (2) by means of PCR, a primer having a nucleotide sequence shown in Sequence ID No. 23 which has a nucleotide sequence that corresponds to the amino acid sequences of TPO and ND28 was synthesized as the 3' side primer (hereinafter referred to as "primer 6").

Using the thus synthesized primer 6 and the primer 1 and pBS-TP0332, PCR was carried out in the following manner.

A 0.1 ml portion of a reaction solution containing 10 ng of pBS-TP0332, 400 nM of the primer 1, 400 nM of the primer 6, 20 mM of Tris-HCl (pH 8.2), 10 mM of potassium chloride, 0.01 mg/ml of BSA, 2 mM of magnesium chloride, 6 mM of ammonium sulfate, 0.1% Triton X-100, 10% DMSO, 0.05 mm of dATP, 0.05 mM of dCTP, 0.05 mM of dGTP and 0.05 mM of dTTP was mixed with 2.5 units of Pfu polymerase to carry out PCR using PERKIN ELMER CETUS DNA Thermal Cycler by 18 time repetition of a three step incubation at 94° C. for 45 seconds, at 50° C. for 1 minute and at 72° C. for 1 minute.

The resulting reaction solution was subjected to phenol/chloroform extraction and ethanol precipitation, and the thus obtained precipitate was dissolved in 0.015 ml of TE buffer.

The thus prepared solution was mixed with restriction enzymes HindIII and XhoI to cleave the DNA amplified by PCR.

The resulting solution was subjected to an agarose gel electrophoresis, and a HindIII-XhoI cleaved DNA fragment of about 0.5 kb was isolated from the agarose gel.

Using DNA Ligation Kit Ver. 1 (manufactured by Takara Shuzo Co., Ltd.), the thus isolated DNA fragment (100 ng) was ligated with a HindIII-XhoI cleaved 2.9 kb fragment (50 ng) of pBlueScript II SK(-) (volume of the reaction solution: 0.018 ml).

Using this reaction solution, the *Escherichia coli* strain DH5α was transformed in the usual way, and the resulting transformant was spread on LB agar medium containing 50 μg/ml of ampicillin and cultivated overnight at 37° C.

Plasmids were isolated from several transformant strains grown on the medium in accordance with a known method.

Nucleotide sequence of the insertion fragment in each plasmid was determined using Taq DyeDeoxy Terminator Cycle Sequencing Kit and ABI373A DNA Sequencer (manufactured by Applied Biosystems Japan Inc.). In determining the nucleotide sequence, primers having the nucleotide sequences of Sequence ID Nos. 9 to 12, 15 and 16 were used as primers for the nucleotide sequence determination.

Determination of nucleotide sequence was carried out in accordance with the instructions attached to the kit and apparatus.

Of the above-mentioned plasmids, plasmid pBS-T154ND in which the nucleotide sequence of the insertion fragment coincided with the nucleotide sequences of the TPO gene and primers was used in the subsequent procedures.

(ii) Preparation of DNA which Codes for TPO-ND28 (2)

The DNA which codes for the TPO moiety prepared in Example 1-2-2)-(i) and the DNA which codes for the ND28 moiety prepared in Example 1-2-1):-(ii) were fused in the following manner.

A 200 ng portion of pBS-T154ND was cleaved with restriction enzymes KpnI and XhoI and subjected to agarose gel electrophoresis to isolate a DNA fragment of about 3.5 kb.

Also, a 500 ng portion of pBS-LND28 was cleaved with restriction enzymes KpnI and XhoI and subjected to agarose gel electrophoresis to isolate a DNA fragment of about 0.5 kb.

Using DNA Ligation Kit Ver. 1 (manufactured by Takara Shuzo Co., Ltd.), the DNA fragment of about 3.5 kb (100 ng) was ligated with the DNA fragment of about 0.5 kb (100 ng) (volume of the reaction solution: 0.018 ml). Using this reaction solution, the *Escherichia coli* strain DH5α was transformed in the usual way, and the resulting transformant was spread on LB agar medium containing 50 μg/ml of ampicillin and cultivated overnight at 37° C.

Plasmids were isolated from several transformant strains grown on the medium in accordance with a known method.

Structures of these plasmids were examined using restriction enzymes KpnII and XhoI, and plasmid pBS-T154ND28 having a structure in which both of the DNA fragments are ligated with each other was used in the subsequent procedures.

3) Construction of DNA (Sequence ID No. 6) which codes for TPO-ND28 (3) [Sequence ID No. 3; a Type Constructed Through a Linker (Ser Gly Gly Gly Ser Gly Gly Gly Ser Gly Gly Gly Ser Gly Gly Gly Arg; Sequence ID No. 24)]

Figure 3:
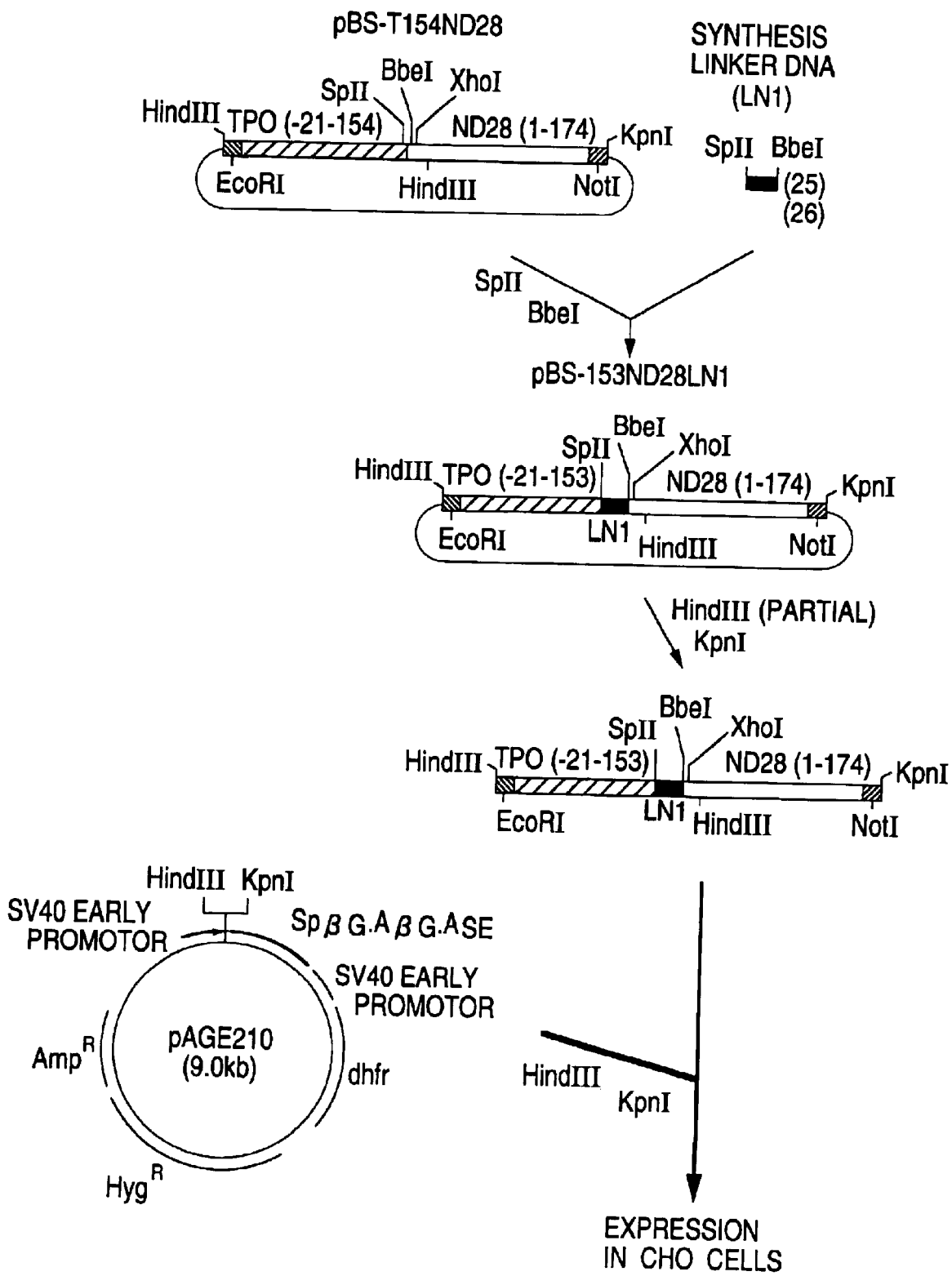
FIG. 3 is an illustration showing construction of a plasmid containing DNA which codes for TPO-ND28 (3).

A DNA which codes for TPO-ND28 (3) in which the 153 amino acids from the N-terminal of TPO, used as its N-terminal side, was fused with the complete length ND28 (174 amino acids) as the C-terminal side through a linker (Ser Gly Gly Gly Ser Gly Gly Gly Ser Gly Gly Gly Ser Gly Gly Gly Arg) was prepared in the following manner (cf. FIG. 3).

In order to ligate the DNA which codes for the TPO moiety prepared in Example 1-2-2)-(i) with the DNA which codes for the ND28 moiety prepared in Example 1-2-1)-(ii) through a linker (Ser Gly Gly Gly Ser Gly Gly Gly Ser Gly Gly Gly Ser Gly Gly Gly Arg), two DNA's shown in Sequence ID Nos. 25 and 26 having nucleotide sequences which form SplI-BbeI complementary termini on both sides corresponding to the amino acid sequences of linkers were synthesized.

A 0.02 ml portion of a solution containing 0.01 mM of the DNA shown in Sequence ID No. 25, 5 mM of ATP, 50 mM of Tris-HCl (pH 8.0), 10 mM of magnesium chloride and 5 mM of dithiothreitol was mixed with 10 units of T4 Polynucleotide Kinase (manufactured by Takara Shuzo Co., Ltd.), and the mixture was allowed to stand at 37° C. for 30 minutes and then heated at 70° C. for 3 minutes to obtain treating solution (1).

The DNA shown in Sequence ID No. 26 was also treated in the same manner to obtain treating solution (2).

Treating solution (1) was mixed with treating solution (2), and the mixture was incubated at 90° C. for 5 minutes and then gradually cooled to 22° C. spending 3 hours to prepare double-stranded DNA.

The thus prepared double-stranded DNA was inserted into the connecting site of the TPO-coding gene and ND28-coding gene of pBS-T154ND28 obtained in Example 1-2-2)-(ii) in the following manner.

A 2,000 ng portion of pBS-T154ND28 was cleaved with restriction enzymes BbeI and SplI and subjected to an agarose gel electrophoresis to isolate a DNA fragment of about 4.0 kb.

Using DNA Ligation Kit Ver. 1 (manufactured by Takara Shuzo Co., Ltd.), the DNA fragment of about 4.0 kb (100 ng) was ligated with the above-mentioned double-stranded DNA (12.5 pmole) (volume of the reaction solution: 0.018 ml).

Using this reaction solution, the *Escherichia coli* strain DH5α was transformed in the usual way, and the resulting transformant was spread on LB agar medium containing 50 μg/ml of ampicillin and cultivated overnight at 37° C.

Plasmids were isolated from several transformant strains grown on the medium in accordance with a known method.

Nucleotide sequence of the insertion fragment in each plasmid was determined using Taq DyeDeoxy Terminator Cycle Sequencing Kit and ABI373A DNA Sequencer. In determining the nucleotide sequence, two DNA's shown in Sequence ID Nos. 12 and 22 were used as primers. Determination of nucleotide sequence was carried out in accordance with the instructions attached to the kit and apparatus.

Of these plasmids, plasmid named pBS-T153ND28LN1 in which the nucleotide sequence of the insertion fragment coincided with the nucleotide sequence of the linker DNA was used in the subsequent procedures.

EXAMPLE 2

Production of TPO-CSF The TPO-CSF was produced by effecting expression of the DNA which codes for the TPO-CSF in animal cells in the following manner.

1) Production of TPO-ND28 (1) and TPO-ND28 (2)

Plasmid pcDNA3 (manufactured by Invitrogen Co.) was cleaved with EcoRI and NotI and subjected to an agarose gel electrophoresis to isolate a DNA fragment (vector side) of about 5.4 kb.

Also, pBS-T153LND28 and pBS-T154ND28 obtained in Example 1-2-1)-(iii) and Example 1-2-2)-(ii) were separately cleaved with EcoRI and NotI and subjected to agarose gel electrophoresis to isolate a DNA fragment (insert side) of about 1.1 kb from each plasmid.

Using DNA Ligation Kit Ver. 1, the vector side DNA fragment of about 5.4 kb (100 ng) was ligated with each of the insert side DNA fragments (100 ng) (volume of the reaction solution: 0.018 ml).

Using this reaction solution, the *Escherichia coli* strain DH5α (was transformed in the usual way, and the resulting transformant was spread on LB agar medium containing 50 μg/ml of ampicillin and cultivated overnight at 37° C.

Plasmids were isolated from several transformant strains grown on the medium in accordance with a known method.

Structure of each plasmid was examined using restriction enzymes EcoRI and NotI to select plasmids containing respective inserts having a structure in which the vector side and insert side DNA fragments are ligated with each other, and plasmid pCD-153LND28 containing a TPO-ND28 (1) encoding gene and plasmid pCD-154ND28 containing a TPO-ND28 (2) encoding gene were used in the subsequent procedure.

Plasmid pCD-153LND28 or pCD-154ND28 was introduced into animal cells by electroporation [Potter et al., *Proc. Natl. Acad. Sci., USA,* 81, 7161 (1984).] and its expression was effected in the following manner.

COS 7 cells were cultivated in D-MEM medium (manufactured by GibcoBRL Co., product No. 11885-50) which was further supplemented with 10% fetal bovine serum.

The COS 7 cells obtained by cultivation were suspended in K-PBS buffer (137 mM potassium chloride, 2.7 mM sodium chloride, 8.1 mM disodium hydrogenphosphate, 1.5 mM sodium dihydrogenphosphate, 4 mM magnesium chloride) to prepare a cell suspension of $8\times10^8$ cells/ml.

A 0.2 ml portion of the cell suspension was injected into a Pulser Cuvette (manufactured by BIO RAD LABORATORIES) having a slit width of 0.2 cm.

A 4 μg portion of pCD-153LND28 or pCD-154ND28 was added to the cuvette, thoroughly mixed with the suspension and then subjected to pulse application using an electroporation apparatus (Gene Pulser, manufactured by BIO RAD LABORATORIES) under conditions of 200 Ω, 0.3 kv/cm and 0.125 mF.

The pulse-treated solution was allowed to stand in ice for 5 minutes, suspended in 10 ml of D-MEM medium supplemented with 10% fetal bovine serum and then cultivated at 37° C. for 72 hours in a $CO_2$ incubator.

The culture broth was subjected to centrifugation, and the resulting culture supernatant was filtered through a filter of 220 nm pore size to obtain a solution of TPO-ND28 (1) or TPO-ND28 (2).

2) Production of TPO-ND28 (3)

A plasmid PAGE210 was used as the vector for use in the expression of TPO-ND28 (3). The vector pAGE210 is a derivative of pAGE248 [Sasaki et al., *J. Biol. Chem.,* 269, 14730, (1994)], in which the Moloney murine leukemia virus promoter (XhoI-HindIII fragment) has been replaced by SV40 early promoter (XhoI-HindIII fragment) of pAGE103 [Mizukami et al., *J. Biochem.,* 101, 1307 (1987)].

Plasmid pAGE210 was cleaved with KpnI and HindIII and subjected to an agarose gel electrophoresis to isolate a DNA fragment (vector side) of about 9.0 kb.

Separately from this, pBS-TP0322 obtained in Example 1-1 was cleaved with KpnI and HindIII, and pBS-153ND28LN1 obtained in Example 1-2-3) was cleaved with KpnI and then partially with HindIII, and each of the resulting cleaved fragments was subjected to an agarose gel electrophoresis to isolate a DNA fragment (insert side) of about 1.1 kb from each plasmid.

Using DNA Ligation Kit Ver. 1, the vector side DNA fragment of about 9.0 kb (100 ng) was ligated with each of the insert side DNA fragments of about 1.1 kb (100 ng) (volume of the reaction solution: 0.012 ml).

Using this reaction solution, the *Escherichia coli* strain DH5α was transformed in the usual way, and the resulting transformant was spread on LB agar medium containing 50 μg/ml of ampicillin and cultivated overnight at 37° C.

Plasmids were isolated from several transformant strains grown on the medium in accordance with a known method.

Structure of each plasmid was examined using a restriction enzyme KpnI to select plasmids containing respective inserts having a structure in which the vector side and insert side DNA fragments are ligated with each other, and plasmid pAGE210-T332 containing TPO encoding gene and plasmid pAGE210-LN1 containing TPO-ND28 (3) encoding gene were used in the subsequent procedure.

Plasmid pAGE210-T332 or pAGE210-LN1 was introduced into animal cells by electroporation.

CHO cells were cultivated in MEM medium (1) (manufactured by GibcoBRL Co., product No. 19000-024) which was further supplemented with 10% fetal bovine serum.

The CHO cells obtained by cultivation were suspended in K-PBS buffer to prepare a cell suspension of $8\times10^6$ cells/ml.

A 0.2 ml portion of the cell suspension was injected into Pulser Cuvette having a slit width of 0.2 cm.

A 4 μg portion of pAGE210-T332 or pAGE210-LN1 was added to the cuvette, thoroughly mixed with the suspension and then subjected to pulse application using an electroporation apparatus, Gene Pulser, under conditions of 0.35 kv/cm and 0.25 mF.

The pulse-treated solution was allowed to stand in ice for 5 minutes, suspended in 10 ml of MEM medium supplemented with 10 fetal bovine serum and then cultivated at 37° C. for 24 hours in a $CO_2$ incubator.

The thus cultivated cells were again cultivated for 2 weeks in MEM medium (1) supplemented with 10% fetal bovine serum and 0.3 mg/ml of hygromycin.

The resulting cells were further cultivated for 2 weeks in MEM medium (2) (manufactured by GibcoBRL Co., code No. 12000-022) supplemented with 10% fetal bovine serum and 50 nM methotrexate (hereinafter referred to as MTX).

The cultivation was repeated in the same manner by successively increasing the MTX concentration to 100 nM, 500 nM and 1,000 nM in that order, thereby obtaining strains resistant to 1,000 nM TMX.

Each of the 1,000 nM MTX resistant strains was grown in MEM medium (2) supplemented with 10% fetal bovine serum, the medium was exchanged with a serum-free medium for CHO cell use, CHO-S-SFMII (manufactured by GibcoBRL Co., code No. 12052-015), and then the strain was cultivated again for 96 to 144 hours.

By subjecting the culture broth to centrifugation, a culture supernatant containing TPO or TPO-ND28 (3) was obtained.

The TPO-ND28 (3) thus modified with polyethylene glycol (hereinafter referred to as PEG-TPO-ND28 (3)) was applied to a column of Super Rose 610/30 (manufactured by Pharmacia K.K.) which has been filled in advance with a phosphate buffer (9.4 mM sodium phosphate (pH 7.2), 137 mM NaCl, 2.7 mM KCl).

Elution was effected by passing the phosphate buffer through the column at a flow rate of 0.5 ml/minute.

The eluates were pooled for every 1 minute, and the resulting fractions were checked for their G-CSF and TPO activities by MTT assay method which will be described later.

The results are shown in Table 5.

The G-CSF and TPO activities originated from un-modified TPO-ND28 (3) were detected 34 to 40 minutes after commencement of the elution, and the G-CSF and TPO activities originated from PEG-TPO-ND28 (3) were detected after 16 to 28 minutes of the elution.

These results confirmed that polyethylene glycol-modified TPO-CSF having both G-CSF and TPO activities can be obtained.

TABLE 5

| Elution time (minutes) | 0 | 10 | 14 | 16 | 18 | 20 | 22 | 24 | 26 | 28 | 30 | 32 | 34 | 36 | 38 | 40 |
|---|---|---|---|---|---|---|---|---|---|---|---|---|---|---|---|---|
| G-CSF activity | − | − | − | + | + | + | + | + | + | + | − | − | + | + | + | + |
| TPO activity | − | − | − | + | + | + | + | + | + | + | − | − | + | + | + | + |

−: no activity;
+: activity

EXAMPLE 3

Purification of TPO-ND28 (3) and TPO

A 1,000 ml portion of TPO-ND28 (3) or TPO obtained in Example 2-2) was concentrated to 50 ml using Centriprep (manufactured by Amicon Co.) to prepare a concentrated solution.

A 50 ml portion of each of the concentrated solutions was applied to XK50 column (manufactured by Pharmacia K.K.) which has been packed with 1,000 ml of Sephacryl S-200 resin (manufactured by Pharmacia K.K.) and filled with a phosphate buffer (9:4 mM sodium phosphate (pH 7.2), 137 mM NaCl, 2.7 mM KCl).

Elution of TPO-ND28 (3) or TPO was effected by passing the phosphate buffer through the column at a flow rate of 3 ml/minute.

The eluates were pooled for every 12.5 minutes, and the resulting fractions were checked for their TPO and G-CSF activities by an MTT assay method which will be described later, thereby obtaining purified TPO-ND28 (3) or TPO.

EXAMPLE 4

Modification of TPO-ND28 (3) with Polyethylene Glycol

To ice-cooled water was added 20 kd PEG-succinimidyl propionate (manufactured by Shearwater Polymers Co.) to a final concentration of 400 mg/ml.

A 50 µl portion of the thus prepared aqueous solution was mixed with 200 µl of the TPO-ND28 (3) solution obtained in Example 3 and 150 µl of distilled water. The mixture was allowed to stand for 12 hours at 4° C., thereby effecting modification of TPO-ND28 (3) by polyethylene glycol.

TEST EXAMPLE 1

Measurement of TPO-ND28 Molecular Weight

Using the TPO-ND28 (1) solution obtained in Example 2-1), its molecular weight was measured by a gel filtration chromatography in the following manner.

A 0.2 ml portion of the TPO-ND28 (1) solution was applied to a column of Super Rose 610/30 (manufactured by Pharmacia K.K.) which has been equilibrated in advance with a phosphate buffer (9.4 mM sodium phosphate (pH 7.2), 137 mM NaCl, 2.7 mM KCl), and elution of TPO-ND28 (1) was effected by passing the phosphate buffer through the column at a flow rate of 0.5 ml/minute.

The eluates were pooled for every 0.5 minute, and the resulting fractions were checked for their TPO and G-CSF activities by an MTT assay method which will be described later.

Table 6 shows elution time from Super Rose and measured values of TPO and G-CSF activities.

The TPO and G-CSF activities reached the maximum after 33.5 minutes of the elution.

Separately from this, thyroglobulin (molecular weight: 670,000), aldolase (molecular weight: 160,000), bovine serum albumin (molecular weights 69,000) and G-CSF (molecular weight: 20,000) were used as the standard molecular weight proteins and passed through Super Rose to obtain relationship between elution time and molecular weight.

Molecular weight of TPO-ND28 (1) deduced from the 33.5 minutes of elution time was about 40,000.

TABLE 6

| Elution time | 0 | 20 | 30 | 32 | 33 | 33.5 | 34 | 35 | 37 | 42 |
|---|---|---|---|---|---|---|---|---|---|---|
| TPO activity ($A_{540}$) | 0.08 | 0.07 | 0.08 | 0.19 | 0.30 | 0.32 | 0.29 | 0.18 | 0.09 | 0.08 |
| G-CSF activity ($A_{540}$) | 0.00 | 0.00 | 0.03 | 0.14 | 0.29 | 0.32 | 0.30 | 0.22 | 0.05 | 0.00 |

TEST EXAMPLE 2

Biological Activity of TPO-CSF

Basic construction for the measurement of the cell growth-stimulating activity of a solution to be tested (TPO-ND28 solution) upon cells to be tested is as follows.

Each solution to be tested (TPO-ND28 solution), TPO standard solution and ND28 standard solution is made into 10-fold serial dilutions, and a 0.01 ml portion of each of the dilutions is added to each well of a microtiter plate.

Actively growing cells to be tested are collected from a culture broth by centrifugation, washed and then re-suspended in a medium for testing use to a most suitable cell density for each testing.

The thus prepared cell suspension is dispensed in 0.09 ml portions into wells of the above-mentioned microtiter plate which has been prepared by dispensing dilutions of the solution to be tested, TPO standard solution or ND28 standard solution in 0.01 ml portions.

The microtiter plate is incubated at 37° C. in a completely moist 5% $CO_2$ incubator and then used in the following testing.

A 0.01 ml portion of 0.5 mg/ml solution of MTT [3-(4, 5-dimethyl-2-thiazolyl)-2,5-diphenyl tetrazolium bromide] is added to each well, incubated for 4 hours, mixed with 0.15 ml of 0.1 N hydrochloric acid/isopropyl alcohol solution and then stirred to extract pigment from the cells, subsequently judging growth of the cells by measuring the amount of the pigment by its absorbance at 540 nm.

This method for the measurement of cell growth-stimulating activity is hereinafter called the MTT assay.

Measurement of Cell Growth-stimulating Activity Upon Ba/F3 Cells

The Ba/F3 cells which grow depending on the presence of mouse IL-3 were cultivated in Iscove's modified Dulbecco medium (hereinafter referred to as "IMDM") which has been supplemented with 10% heat-inactivated fetal calf serum (hereinafter referred to as "FCS") and mouse IL-3 (culture supernatant of WEHI-3B).

Using the thus cultivated Ba/F3 cells, the cell growth-stimulating activity was measured by the MTT assay using the just described medium but in the absence of mouse IL-3.

The MTT assay was carried out with an inoculation density of 10,000 cells per well and by incubating the plate in 5% $CO_2$ for 48 hours.

Results of the MTT assay showed that each of TPO, ND28 and TPO-ND28 (1), (2) and (3) had no Ba/F3 cell growth-stimulating activity.

(2) Measurement of Cell Growth-stimulating Activity Upon Ba/F3-cmpl

The Ba/F3-cmpl cells which grow depending on the presence of mouse IL-3 or TPO were cultivated in IMDM which has been supplemented with 10% heat-inactivated FCS, 0.5 mg/ml of G418 and mouse IL-3 (culture supernatant of WEHI-3B).

Using the thus cultivated Ba/F3-cmpl cells, the cell growth-stimulating activity was measured by MTT assay using the just described medium but in the absence of mouse IL-3.

The MTT assay was carried out with an inoculation density of 10,000 cells per well and by incubating the plate in 5% $CO_2$ for 48 hours.

Results of the MTT assay showed that each of TPO and TPO-ND28 (1), (2) and (3) had Ba/F3-cmp cell growth-stimulating activity.

(3) Measurement of Cell Growth-stimulating Activity Upon NFS-60 cells

The NFS-60 cells which grow depending on the presence of human G-CSF or mouse IL-3 were cultivated in RPMI medium which has been supplemented with 10% heat-inactivated FCS, 2 mM glutamine, P/S (100 U/ml of penicillin, 100 mg/ml of streptomycin) and 1.0 ng/ml of recombinant type human G-CSF.

Using the thus cultivated NFS-60 cells, the cell growth-stimulating activity was measured by the MTT assay using the just described medium but in the absence of G-CSF.

The MTT assay was carried out with an inoculation density of 10,000 cells per well and by incubating the plate in 5% $CO_2$ for 48 hours.

Results of the MTT assay showed that each of ND28 and TPO-ND28 (1), (2) and (3) had NFS-60 cell growth-stimulating activity.

TEST EXAMPLE 3

Effect of TPO-ND28 on Mouse Myeloid Cells

A BALB/c mouse of 8 weeks of age was sacrificed to excise the femur and tibia system whose both ends were subsequently cut with scissors. The needle of a syringe filled with RPMI solution containing 10% FCS was inserted into the section of femur and tibis to blow off myeloid cells into a small test tube, and the cells were allowed to stand for 5 minutes.

Using a Pasteur pipette, the supernatant fluid in the test tube was drawn up taking care not to contaminate it with the precipitate, and the supernatant fluid was overlaid on Nycoprep 1.077 Animal (manufactured by NYCONED Co., product No. 1002380) and subjected to 15 minutes of centrifugation at 600 g to isolate mouse mono nuclear cells (hereinafter referred to as "MNC").

The MNC were made into a suspension of $5 \times 10^5$ cells/ml with a solution containing a solution to be tested, 10% FCS, 1% BSA and 0.6 mg/ml of transferrin (manufactured by Boehringer Manheim Co.) and cultivated for 5 days in a $CO_2$ incubator (BNA-120D, manufactured by TABAI Co.) under conditions of 37° C., 5% $CO_2$ and 95% or more of humidity.

As the solution to be tested, a solution of TPO, ND28 or TPO-ND28 having a final concentration of 1.0, 10 or 100 ng/ml or a solution in which the same volume of TPO and ND-28 solutions having the above-mentioned concentration were mixed (TPO/ND28) was used. The TPO and ND28 obtained in Example 3 were used.

After completion of the cultivation, conditions of the differentiation of MNC were examined by measuring the amount of CD61 expressed which is an index of differentiation into megakaryocyte system [*J. Med.*, 311, 1084 (1984)] and the amount of Gr-1 expressed which is an index of differentiation into the granulocyte system [*J. Immunol.*, 144, 22 (1991)].

After staining with anti mouse CD61-FITC monoclonal antibody (manufactured by PHARMINGEN Co., product No. 01864D) and anti mouse Gr-1-PE monoclonal antibody (manufactured by PHARMINGEN Co., product No. 01215A), expressed amounts of CD61 and Gr-1 were measured using an ELITE flow cytometer (manufactured by Coulter Co.).

The results are shown in Table 7.

TABLE 7

| Solution to be tested | Concentration (ng/ml) | Expressed cells (%) | |
|---|---|---|---|
| | | Gr-1 | CD61 |
| no addition | | 1.0 | 1.0 |
| ND28 | 1.0 | 49.1 | 7.6 |
| | 10.0 | 40.7 | 4.9 |
| | 100.0 | 44.5 | 4.6 |
| TPO | 1.0 | 36.7 | 8.7 |
| | 10.0 | 37.7 | 17.8 |
| | 100.0 | 37.1 | 21.9 |
| TPO/ND28 | 1.0 | 50.7 | 10.3 |
| | 10.0 | 40.6 | 10.4 |
| | 100.0 | 49.2 | 5.7 |
| TPO-ND28 | 1.0 | 50.5 | 22.1. |
| | 10.0 | 49.8 | 26.6 |
| | 100.0 | 41.0 | 18.8 |

When the solution to be tested prepared by mixing the same amount of TPO and ND28 (TPO/ND28) was added, Gr-1 expressed cells were generated in a level similar to the case of the addition of the solution to be tested containing ND28 alone, thus showing differentiation of MNC into the granulocyte system, but frequency of the generation of CD61 expressed cells was lower than the case of the addition of the solution to be tested containing TPO alone, thus showing decreased differentiation into the megakaryocyte system. These results suggest that, when the same amount of TPO and ND28 are present, MNC reacts mostly with ND28 and differentiates into the granulocyte system.

However, when the fusion polypeptide of TPO and ND28, namely TPO-ND28, was added as the solution to be tested, frequency of the generation of CD61 expressed cells was similar to or higher than the case of the addition of the solution to be tested containing TPO alone and two times or more higher than the case of the addition of TPO/ND28. What is more, the frequency of the generation of Gr-1 expressed cells was also similar to the case of the addition of the solution to be tested containing ND28 alone.

TEST EXAMPLE 4

Platelet and Leukocyte Production-enhancing Function in Mice

A 10 μg/ml solution of TPO or a 10 μg/ml solution of TPO-ND28 (3) obtained in Example 3 was administered by subcutaneous injection to BALB/c mice (males, 7 weeks of age) with a dose of 0.2 ml per 20 g body weight of each mouse, once a day continuously for 4 days starting on the first day of the test (treated groups, 4 animals per one group). A blood sample was collected from the ophthalmic vein of each animal on the fifth day of the test to count the number of platelets and leukocytes by a microcell counter (Sysmex F800, manufactured by To a Iyo Denshi Co.).

After introducing the plasmid pAGE210 used for the expression of TPO or TPO-ND28 (3) gene into CHO cells in accordance with the method described in Example 2-2), the cells were cultivated, the resulting culture supernatant was treated by the same TPO-ND28 (3) purification procedure described in Example 3, and an elution fraction corresponding to the elution fraction of TPO-ND28 (3) was used as a blank solution to count the number of platelets and leukocytes by the above-mentioned method.

In order to compare and examine effects of TPO and TPO-ND28 (3), the increasing ratio (%) of the number of platelets and leukocytes in the group in which each of these substances were administered to that in the blank solution-administered group was calculated based on the following formula:

[platelet or leukocyte counts in mice of TPO- or TPO-ND28 (3)-administered group]/[platelet or leukocyte count in mice of blank solution-administered group]×100

The results are shown in Table 8.

TABLE 8

| Test substance | Increasing ratio of platelets (%) | Increasing ratio of leukocytes (%) |
|---|---|---|
| TPO | 219 | 106 |
| TPO-ND28 | 170 | 160 |

INDUSTRIAL APPLICABILITY

A fusion polypeptide comprising a polypeptide having both G-CSF activity and a polypeptide having TPO activity is provided by the present invention. The fusion polypeptide of the present invention can form and amplify platelets and leukocytes simultaneously and can control formation of megakaryocyte colonies and neutrophil colonies and differentiation or maturation of megakaryocyte precursors and neutrophil precursors.

What is claimed is:

1. A fusion polypeptide which comprises a human granulocyte colony stimulating factor polypeptide and c-mpl ligand polypeptide and has no mouse IL-3 activity as measured by inability to stimulate growth of Ba/F3 cells, wherein the polypeptide comprises the amino acid sequence shown in SEQ ID NO:1 or an amino acid sequence in which the amino acid nos. 155 to 328 of the amino acid sequence shown in SEQ ID NO:1 Is replaced by an amino acid sequence of SEQ ID NO:39 or by an amino acid sequence in which the amino acid nos. 155 to 328 of the amino acid sequence shown in SEQ ID NO:1 is replaced by an amino acid sequence of SEQ ID NO:46 having a set of substitutions selected from the group consisting of those of Table 2 a) to j) and l).

2. The fusion polypeptide of claim 1 chemically modified with a polyalkylene glycol derivative.

3. The fusion polypeptide according to claim 2 wherein the polyalkylene glycol derivative is a polyethylene glycol derivative, a polypropylene glycol derivative or a polyoxyethylene-polyoxypropylene copolymer derivative.

4. A pharmaceutical composition for treating anemia comprising the fusion polypeptide of claim 1 in a pharmaceutically acceptable carrier, vehicle or auxiliary agent.

5. A method of treating anemia comprising administering to a subject in need of same an effective amount of the fusion polypeptide of claim 1.

6. A method of simultaneously amplifying platelets and neutrophils comprising administering to a subject in need of same an effective amount of the fusion polypeptide of claim 1.

7. A method of controlling differentiation or maturation of megakaryocyte precursors and neutrophil precursors comprising administering to a subject in need of same an effective amount of the fusion polypeptide of claim 1.

8. A fusion polypeptide which comprises a human granulocyte colony stimulating factor polypeptide and c-mpl ligand polypeptide and has no mouse IL-3 activity as measured by inability to stimulate growth of Ba/F3 cells, wherein the polypeptide comprises the amino acid sequence shown In SEQ ID NO:1 or an amino acid sequence in which the amino acid nos. 155 to 328 of the amino acid sequence shown in SEQ ID NO:1 is replaced by an amino acid sequence of SEQ ID NO:39 or by an amino acid sequence in which the amino acid nos. 155 to 328 of the amino acid sequence shown in SEQ ID NO:1 is replaced by an amino acid sequence of SEQ ID NO:46 having a set of substitutions selected from the group consisting of those of j) and l), and the human granulocyte colony stimulating factor polypeptide is fused via a spacer peptide to the c-mpl ligand polypeptide.

9. The fusion polypeptide according to claim 8, wherein the polypeptide is selected from a polypeptide comprising the amino acid sequence shown in SEQ ID NO:2 or SEQ ID NO:3, an amino acid sequence in which the amino acid nos. 167 to 340 of the amino acid sequence shown in SEQ ID NO:2 is replaced by an amino acid sequence of SEQ ID NO:39 or by an amino acid sequence in which the amino acid nos. 167 to 340 of the amino acid sequence shown in SEQ ID NO:2 is replaced by an amino acid sequence of SEQ ID NO:46 having a set of substitutions selected from the group consisting of those of Table 2 a) to j) and l), and an amino acid sequence in which the amino acid nos. 171 to 344 of the amino acid sequence shown in SEQ ID NO: 3 is replaced by an amino acid sequence of SEQ ID NO:39 or by an amino acid sequence in which the amino acid nos. 171 to 344 of the amino acid sequence shown in SEQ ID NO:3 is replaced by an amino acid sequence of SEQ ID NO:46 having a set of substitutions selected from the group consisting of those of Table 2 a) to j) and l).

* * * * *

SEQUENCE LISTING (1) GENERAL INFORMATION:

(iii) NUMBER OF SEQUENCES: 46

(2) INFORMATION FOR SEQ ID NO: 1:

(i) SEQUENCE CHARACTERISTICS:
        (A) LENGTH: 328 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 1:

```
Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
        50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                    100                 105                 110

Pro Pro Gln Gly Arg Thr Thr Ala His Lys Asp Pro Asn Ala Ile Phe
                115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Thr Tyr Arg Ala
145                 150                 155                 160

Ser Ser Leu Pro Gln Ser Phe Leu Leu Lys Ser Leu Glu Gln Val Arg
                165                 170                 175

Lys Ile Gln Gly Asp Gly Ala Ala Leu Gln Glu Lys Leu Cys Ala Thr
                180                 185                 190

Tyr Lys Leu Cys His Pro Glu Glu Leu Val Leu Leu Gly His Ser Leu
            195                 200                 205

Gly Ile Pro Trp Ala Pro Leu Ser Ser Cys Pro Ser Gln Ala Leu Gln
210                 215                 220

Leu Ala Gly Cys Leu Ser Gln Leu His Ser Gly Leu Phe Leu Tyr Gln
225                 230                 235                 240

Gly Leu Leu Gln Ala Leu Glu Gly Ile Ser Pro Glu Leu Gly Pro Thr
                245                 250                 255

Leu Asp Thr Leu Gln Leu Asp Val Ala Asp Phe Ala Thr Thr Ile Trp
                260                 265                 270

Gln Gln Met Glu Glu Leu Gly Met Ala Pro Ala Leu Gln Pro Thr Gln
            275                 280                 285

Gly Ala Met Pro Ala Phe Ala Ser Ala Phe Gln Arg Arg Ala Gly Gly
            290                 295                 300

Val Leu Val Ala Ser His Leu Gln Ser Phe Leu Glu Val Ser Tyr Arg
305                 310                 315                 320

Val Leu Arg His Leu Ala Gln Pro
                325
```

(2) INFORMATION FOR SEQ ID NO: 2:

(i) SEQUENCE CHARACTERISTICS:
        (A) LENGTH: 340 amino acids (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 2:

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
        50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
                100                 105                 110

Pro Pro Gln Gly Arg Thr Thr Ala His Lys Asp Pro Asn Ala Ile Phe
                115                 120                 125

Leu Ser Phe Gln His Leu Leu Arg Gly Lys Val Arg Phe Leu Met Leu
130                 135                 140

Val Gly Gly Ser Thr Leu Cys Val Arg Gly Gly Ser Gly Gly Gly
145                 150                 155                 160

Ser Gly Gly Gly Ser Arg Ala Pro Thr Tyr Arg Ala Ser Ser Leu Pro
                165                 170                 175

Gln Ser Phe Leu Leu Lys Ser Leu Glu Gln Val Arg Lys Ile Gln Gly
                180                 185                 190

Asp Gly Ala Ala Leu Gln Glu Lys Leu Cys Ala Thr Tyr Lys Leu Cys
                195                 200                 205

His Pro Glu Glu Leu Val Leu Leu Gly His Ser Leu Gly Ile Pro Trp
            210                 215                 220

Ala Pro Leu Ser Ser Cys Pro Ser Gln Ala Leu Gln Leu Ala Gly Cys
225                 230                 235                 240

Leu Ser Gln Leu His Ser Gly Leu Phe Leu Tyr Gln Gly Leu Leu Gln
                245                 250                 255

Ala Leu Glu Gly Ile Ser Pro Glu Leu Gly Pro Thr Leu Asp Thr Leu
                260                 265                 270

Gln Leu Asp Val Ala Asp Phe Ala Thr Thr Ile Trp Gln Gln Met Glu
                275                 280                 285

Glu Leu Gly Met Ala Pro Ala Leu Gln Pro Thr Gln Gly Ala Met Pro
            290                 295                 300

Ala Phe Ala Ser Ala Phe Gln Arg Arg Ala Gly Gly Val Leu Val Ala
305                 310                 315                 320

Ser His Leu Gln Ser Phe Leu Glu Val Ser Tyr Arg Val Leu Arg His
                325                 330                 335

Leu Ala Gln Pro
        340

(2) INFORMATION FOR SEQ ID NO: 3:

(i) SEQUENCE CHARACTERISTICS:
        (A) LENGTH: 344 amino acids

```
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 3:

Ser Pro Ala Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
 50                  55                  60

Gly Ala Val Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
               100                 105                 110

Pro Pro Gln Gly Arg Thr Thr Ala His Lys Asp Pro Asn Ala Ile Phe
               115                 120                 125

Leu Ser Phe Gln His Leu Leu Arg Gly Lys Val Arg Phe Leu Met Leu
 130                 135                 140

Val Gly Gly Ser Thr Leu Cys Val Arg Ser Gly Gly Gly Ser Gly Gly
 145                 150                 155                 160

Gly Ser Gly Gly Gly Ser Gly Gly Gly Arg Ala Pro Thr Tyr Arg Ala
                 165                 170                 175

Ser Ser Leu Pro Gln Ser Phe Leu Leu Lys Ser Leu Glu Gln Val Arg
             180                 185                 190

Lys Ile Gln Gly Asp Gly Ala Ala Leu Gln Glu Lys Leu Cys Ala Thr
             195                 200                 205

Tyr Lys Leu Cys His Pro Glu Glu Leu Val Leu Leu Gly His Ser Leu
 210                 215                 220

Gly Ile Pro Trp Ala Pro Leu Ser Ser Cys Pro Ser Gln Ala Leu Gln
 225                 230                 235                 240

Leu Ala Gly Cys Leu Ser Gln Leu His Ser Gly Leu Phe Leu Tyr Gln
                 245                 250                 255

Gly Leu Leu Gln Ala Leu Glu Gly Ile Ser Pro Glu Leu Gly Pro Thr
             260                 265                 270

Leu Asp Thr Leu Gln Leu Asp Val Ala Asp Phe Ala Thr Thr Ile Trp
             275                 280                 285

Gln Gln Met Glu Glu Leu Gly Met Ala Pro Ala Leu Gln Pro Thr Gln
 290                 295                 300

Gly Ala Met Pro Ala Phe Ala Ser Ala Phe Gln Arg Arg Ala Gly Gly
 305                 310                 315                 320

Val Leu Val Ala Ser His Leu Gln Ser Phe Leu Glu Val Ser Tyr Arg
                 325                 330                 335

Val Leu Arg His Leu Ala Gln Pro
             340

(2) INFORMATION FOR SEQ ID NO: 4:

(i) SEQUENCE CHARACTERISTICS:
        (A) LENGTH: 1047 base pairs
```

-continued (B) TYPE: nucleic acid
(C) STRANDEDNESS: double
(D) TOPOLOGY: linear (ii) MOLECULE TYPE: other nucleic acid
    (A) DESCRIPTION: /desc = "synthetic DNA"

(ix) FEATURE:
    (A) NAME/KEY: sig_peptide
    (B) LOCATION: 1..63

(ix) FEATURE:
    (A) NAME/KEY: mat_peptide
    (B) LOCATION: 64..1047

(ix) FEATURE:
    (A) NAME/KEY: CDS
    (B) LOCATION: 1..1047

(xi) SEQUENCE DESCRIPTION: SEQ ID NO: 4:

```
ATG GAG CTG ACT GAA TTG CTC CTC GTG GTC ATG CTT CTC CTA ACT GCA      48
Met Glu Leu Thr Glu Leu Leu Leu Val Val Met Leu Leu Leu Thr Ala
-21 -20             -15                 -10

AGG CTA ACG CTG TCC AGC CCG GCT CCT CCT GCT TGT GAC CTC CGA GTC      96
Arg Leu Thr Leu Ser Ser Pro Ala Pro Pro Ala Cys Asp Leu Arg Val
-5                1               5                   10

CTC AGT AAA CTG CTT CGT GAC TCC CAT GTC CTT CAC AGC AGA CTG AGC     144
Leu Ser Lys Leu Leu Arg Asp Ser His Val Leu His Ser Arg Leu Ser
            15                  20                  25

CAG TGC CCA GAG GTT CAC CCT TTG CCT ACA CCT GTC CTG CTG CCT GCT     192
Gln Cys Pro Glu Val His Pro Leu Pro Thr Pro Val Leu Leu Pro Ala
        30                  35                  40

GTG GAC TTT AGC TTG GGA GAA TGG AAA ACC CAG ATG GAG GAG ACC AAG     240
Val Asp Phe Ser Leu Gly Glu Trp Lys Thr Gln Met Glu Glu Thr Lys
    45                  50                  55

GCA CAG GAC ATT CTG GGA GCA GTG ACC CTT CTG CTG GAG GGA GTG ATG     288
Ala Gln Asp Ile Leu Gly Ala Val Thr Leu Leu Leu Glu Gly Val Met
60                  65                  70                  75

GCA GCA CGG GGA CAA CTG GGA CCC ACT TGC CTC TCA TCC CTC CTG GGG     336
Ala Ala Arg Gly Gln Leu Gly Pro Thr Cys Leu Ser Ser Leu Leu Gly
                80                  85                  90

CAG CTT TCT GGA CAG GTC CGT CTC CTC CTT GGG GCC CTG CAG AGC CTC     384
Gln Leu Ser Gly Gln Val Arg Leu Leu Leu Gly Ala Leu Gln Ser Leu
            95                  100                 105

CTT GGA ACC CAG CTT CCT CCA CAG GGC AGG ACC ACA GCT CAC AAG GAT     432
Leu Gly Thr Gln Leu Pro Pro Gln Gly Arg Thr Thr Ala His Lys Asp
        110                 115                 120

CCC AAT GCC ATC TTC CTG AGC TTC CAA CAC CTG CTC CGA GGA AAG GTG     480
Pro Asn Ala Ile Phe Leu Ser Phe Gln His Leu Leu Arg Gly Lys Val
    125                 130                 135

CGT TTC CTG ATG CTT GTA GGA GGG TCC ACC CTC TGC GTA CGG CGG GCG     528
Arg Phe Leu Met Leu Val Gly Gly Ser Thr Leu Cys Val Arg Arg Ala
140                 145                 150                 155

CCA ACA TAT CGC GCC TCG AGT CTA CCA CAG AGC TTC CTT TTA AAA AGC     576
Pro Thr Tyr Arg Ala Ser Ser Leu Pro Gln Ser Phe Leu Leu Lys Ser
                160                 165                 170

TTA GAG CAA GTG AGG AAG ATC CAG GGC GAT GGC GCA GCG CTC CAG GAG     624
Leu Glu Gln Val Arg Lys Ile Gln Gly Asp Gly Ala Ala Leu Gln Glu
            175                 180                 185

AAG CTG TGT GCC ACC TAC AAG CTG TGC CAC CCC GAG GAG CTG GTG CTG     672
Lys Leu Cys Ala Thr Tyr Lys Leu Cys His Pro Glu Glu Leu Val Leu
        190                 195                 200

CTC GGA CAC TCT CTG GGC ATC CCC TGG GCT CCC CTG AGC AGC TGC CCC     720
Leu Gly His Ser Leu Gly Ile Pro Trp Ala Pro Leu Ser Ser Cys Pro
```

-continued

```
            205                 210                 215
AGC CAG GCC CTG CAG CTG GCA GGC TGC TTG AGC CAA CTC CAT AGC GGC      768
Ser Gln Ala Leu Gln Leu Ala Gly Cys Leu Ser Gln Leu His Ser Gly
220                 225                 230                 235

CTT TTC CTC TAC CAG GGG CTC CTG CAG GCC CTG GAA GGG ATC TCC CCC      816
Leu Phe Leu Tyr Gln Gly Leu Leu Gln Ala Leu Glu Gly Ile Ser Pro
                240                 245                 250

GAG TTG GGT CCC ACC TTG GAC ACA CTG CAG CTG GAC GTC GCC GAC TTT      864
Glu Leu Gly Pro Thr Leu Asp Thr Leu Gln Leu Asp Val Ala Asp Phe
            255                 260                 265

GCC ACC ACC ATC TGG CAG CAG ATG GAA GAA CTG GGA ATG GCC CCT GCC      912
Ala Thr Thr Ile Trp Gln Gln Met Glu Glu Leu Gly Met Ala Pro Ala
        270                 275                 280

CTG CAG CCC ACC CAG GGT GCC ATG CCG GCC TTC GCC TCT GCT TTC CAG      960
Leu Gln Pro Thr Gln Gly Ala Met Pro Ala Phe Ala Ser Ala Phe Gln
    285                 290                 295

CGC CGG GCA GGA GGG GTC CTA GTT GCC TCC CAT CTG CAG AGC TTC CTG     1008
Arg Arg Ala Gly Gly Val Leu Val Ala Ser His Leu Gln Ser Phe Leu
300                 305                 310                 315

GAG GTG TCG TAC CGC GTT CTA CGC CAC CTT GCC CAG CCC                 1047
Glu Val Ser Tyr Arg Val Leu Arg His Leu Ala Gln Pro
                320                 325
```

(2) INFORMATION FOR SEQ ID NO: 5:

(i) SEQUENCE CHARACTERISTICS:
        (A) LENGTH: 349 amino acids
        (B) TYPE: amino acid
        (D) TOPOLOGY: linear (ii) MOLECULE TYPE: protein (xi) SEQUENCE DESCRIPTION: SEQ ID NO: 5:

```
Met Glu Leu Thr Glu Leu Leu Leu Val Val Met Leu Leu Thr Ala
-21 -20                 -15                 -10

Arg Leu Thr Leu Ser Ser Pro Ala Pro Pro Ala Cys Asp Leu Arg Val
-5                  1                   5                  10

Leu Ser Lys Leu Leu Arg Asp Ser His Val Leu His Ser Arg Leu Ser
                15                  20                  25

Gln Cys Pro Glu Val His Pro Leu Pro Thr Pro Val Leu Leu Pro Ala
            30                  35                  40

Val Asp Phe Ser Leu Gly Glu Trp Lys Thr Gln Met Glu Glu Thr Lys
        45                  50                  55

Ala Gln Asp Ile Leu Gly Ala Val Thr Leu Leu Leu Glu Gly Val Met
60                  65                  70                  75

Ala Ala Arg Gly Gln Leu Gly Pro Thr Cys Leu Ser Ser Leu Leu Gly
                80                  85                  90

Gln Leu Ser Gly Gln Val Arg Leu Leu Leu Gly Ala Leu Gln Ser Leu
            95                  100                 105

Leu Gly Thr Gln Leu Pro Pro Gln Gly Arg Thr Thr Ala His Lys Asp
        110                 115                 120

Pro Asn Ala Ile Phe Leu Ser Phe Gln His Leu Leu Arg Gly Lys Val
    125                 130                 135

Arg Phe Leu Met Leu Val Gly Gly Ser Thr Leu Cys Val Arg Arg Ala
140                 145                 150                 155

Pro Thr Tyr Arg Ala Ser Ser Leu Pro Gln Ser Phe Leu Leu Lys Ser
                160                 165                 170

Leu Glu Gln Val Arg Lys Ile Gln Gly Asp Gly Ala Ala Leu Gln Glu
```

```
                    175                 180                 185
Lys Leu Cys Ala Thr Tyr Lys Leu Cys His Pro Glu Glu Leu Val Leu
                190                 195                 200

Leu Gly His Ser Leu Gly Ile Pro Trp Ala Pro Leu Ser Ser Cys Pro
            205                 210                 215

Ser Gln Ala Leu Gln Leu Ala Gly Cys Leu Ser Gln Leu His Ser Gly
220                 225                 230                 235

Leu Phe Leu Tyr Gln Gly Leu Leu Gln Ala Leu Glu Gly Ile Ser Pro
                240                 245                 250

Glu Leu Gly Pro Thr Leu Asp Thr Leu Gln Leu Asp Val Ala Asp Phe
            255                 260                 265

Ala Thr Thr Ile Trp Gln Gln Met Glu Glu Leu Gly Met Ala Pro Ala
            270                 275                 280

Leu Gln Pro Thr Gln Gly Ala Met Pro Ala Phe Ala Ser Ala Phe Gln
            285                 290                 295

Arg Arg Ala Gly Gly Val Leu Val Ala Ser His Leu Gln Ser Phe Leu
300                 305                 310                 315

Glu Val Ser Tyr Arg Val Leu Arg His Leu Ala Gln Pro
                320                 325

(2) INFORMATION FOR SEQ ID NO: 6:

(i) SEQUENCE CHARACTERISTICS:
        (A) LENGTH: 1083 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA"

(ix) FEATURE:
        (A) NAME/KEY: sig_peptide
        (B) LOCATION: 1..63

(ix) FEATURE:
        (A) NAME/KEY: mat_peptide
        (B) LOCATION: 64..1083

(ix) FEATURE:
        (A) NAME/KEY: CDS
        (B) LOCATION: 1..1083

(xi) SEQUENCE DESCRIPTION: SEQ ID NO: 6:

ATG GAG CTG ACT GAA TTG CTC CTC GTG GTC ATG CTT CTC CTA ACT GCA      48
Met Glu Leu Thr Glu Leu Leu Leu Val Val Met Leu Leu Leu Thr Ala
-21 -20                 -15                 -10

AGG CTA ACG CTG TCC AGC CCG GCT CCT CCT GCT TGT GAC CTC CGA GTC      96
Arg Leu Thr Leu Ser Ser Pro Ala Pro Pro Ala Cys Asp Leu Arg Val
 -5                   1                   5                  10

CTC AGT AAA CTG CTT CGT GAC TCC CAT GTC CTT CAC AGC AGA CTG AGC     144
Leu Ser Lys Leu Leu Arg Asp Ser His Val Leu His Ser Arg Leu Ser
                 15                  20                  25

CAG TGC CCA GAG GTT CAC CCT TTG CCT ACA CCT GTC CTG CTG CCT GCT     192
Gln Cys Pro Glu Val His Pro Leu Pro Thr Pro Val Leu Leu Pro Ala
             30                  35                  40

GTG GAC TTT AGC TTG GGA GAA TGG AAA ACC CAG ATG GAG GAG ACC AAG     240
Val Asp Phe Ser Leu Gly Glu Trp Lys Thr Gln Met Glu Glu Thr Lys
         45                  50                  55

GCA CAG GAC ATT CTG GGA GCA GTG ACC CTT CTG CTG GAG GGA GTG ATG     288
Ala Gln Asp Ile Leu Gly Ala Val Thr Leu Leu Leu Glu Gly Val Met
 60                  65                  70                  75
```

| | | |
|---|---|---|
| GCA GCA CGG GGA CAA CTG GGA CCC ACT TGC CTC TCA TCC CTC CTG GGG<br>Ala Ala Arg Gly Gln Leu Gly Pro Thr Cys Leu Ser Ser Leu Leu Gly<br>80 85 90 | | 336 |
| CAG CTT TCT GGA CAG GTC CGT CTC CTC CTT GGG GCC CTG CAG AGC CTC<br>Gln Leu Ser Gly Gln Val Arg Leu Leu Leu Gly Ala Leu Gln Ser Leu<br>95 100 105 | | 384 |
| CTT GGA ACC CAG CTT CCT CCA CAG GGC AGG ACC ACA GCT CAC AAG GAT<br>Leu Gly Thr Gln Leu Pro Pro Gln Gly Arg Thr Thr Ala His Lys Asp<br>110 115 120 | | 432 |
| CCC AAT GCC ATC TTC CTG AGC TTC CAA CAC CTG CTC CGA GGA AAG GTG<br>Pro Asn Ala Ile Phe Leu Ser Phe Gln His Leu Leu Arg Gly Lys Val<br>125 130 135 | | 480 |
| CGT TTC CTG ATG CTT GTA GGA GGG TCC ACC CTC TGC GTC AGG GGT GGC<br>Arg Phe Leu Met Leu Val Gly Gly Ser Thr Leu Cys Val Arg Gly Gly<br>140 145 150 155 | | 528 |
| GGT TCT GGA GGT GGT TCC GGA GGG GGT TCT AGA GCA CCA ACA TAT CGC<br>Gly Ser Gly Gly Gly Ser Gly Gly Gly Ser Arg Ala Pro Thr Tyr Arg<br>160 165 170 | | 576 |
| GCC TCG AGT CTA CCA CAG AGC TTC CTT TTA AAA AGC TTA GAG CAA GTG<br>Ala Ser Ser Leu Pro Gln Ser Phe Leu Leu Lys Ser Leu Glu Gln Val<br>175 180 185 | | 624 |
| AGG AAG ATC CAG GGC GAT GGC GCA GCG CTC CAG GAG AAG CTG TGT GCC<br>Arg Lys Ile Gln Gly Asp Gly Ala Ala Leu Gln Glu Lys Leu Cys Ala<br>190 195 200 | | 672 |
| ACC TAC AAG CTG TGC CAC CCC GAG GAG CTG GTG CTG CTC GGA CAC TCT<br>Thr Tyr Lys Leu Cys His Pro Glu Glu Leu Val Leu Leu Gly His Ser<br>205 210 215 | | 720 |
| CTG GGC ATC CCC TGG GCT CCC CTG AGC AGC TGC CCC AGC CAG GCC CTG<br>Leu Gly Ile Pro Trp Ala Pro Leu Ser Ser Cys Pro Ser Gln Ala Leu<br>220 225 230 235 | | 768 |
| CAG CTG GCA GGC TGC TTG AGC CAA CTC CAT AGC GGC CTT TTC CTC TAC<br>Gln Leu Ala Gly Cys Leu Ser Gln Leu His Ser Gly Leu Phe Leu Tyr<br>240 245 250 | | 816 |
| CAG GGG CTC CTG CAG GCC CTG GAA GGG ATC TCC CCC GAG TTG GGT CCC<br>Gln Gly Leu Leu Gln Ala Leu Glu Gly Ile Ser Pro Glu Leu Gly Pro<br>255 260 265 | | 864 |
| ACC TTG GAC ACA CTG CAG CTG GAC GTC GCC GAC TTT GCC ACC ACC ATC<br>Thr Leu Asp Thr Leu Gln Leu Asp Val Ala Asp Phe Ala Thr Thr Ile<br>270 275 280 | | 912 |
| TGG CAG CAG ATG GAA GAA CTG GGA ATG GCC CCT GCC CTG CAG CCC ACC<br>Trp Gln Gln Met Glu Glu Leu Gly Met Ala Pro Ala Leu Gln Pro Thr<br>285 290 295 | | 960 |
| CAG GGT GCC ATG CCG GCC TTC GCC TCT GCT TTC CAG CGC CGG GCA GGA<br>Gln Gly Ala Met Pro Ala Phe Ala Ser Ala Phe Gln Arg Arg Ala Gly<br>300 305 310 315 | | 1008 |
| GGG GTC CTA GTT GCC TCC CAT CTG CAG AGC TTC CTG GAG GTG TCG TAC<br>Gly Val Leu Val Ala Ser His Leu Gln Ser Phe Leu Glu Val Ser Tyr<br>320 325 330 | | 1056 |
| CGC GTT CTA CGC CAC CTT GCC CAG CCC<br>Arg Val Leu Arg His Leu Ala Gln Pro<br>335 340 | | 1083 |

(2) INFORMATION FOR SEQ ID NO: 7:

(i) SEQUENCE CHARACTERISTICS:
        (A) LENGTH: 361 amino acids
        (B) TYPE: amino acid
        (D) TOPOLOGY: linear (ii) MOLECULE TYPE: protein (xi) SEQUENCE DESCRIPTION: SEQ ID NO: 7:

```
Met Glu Leu Thr Glu Leu Leu Val Val Met Leu Leu Thr Ala
-21 -20          -15             -10

Arg Leu Thr Leu Ser Ser Pro Ala Pro Pro Ala Cys Asp Leu Arg Val
 -5              1           5                       10

Leu Ser Lys Leu Leu Arg Asp Ser His Val Leu His Ser Arg Leu Ser
         15              20              25

Gln Cys Pro Glu Val His Pro Leu Pro Thr Pro Val Leu Leu Pro Ala
         30              35              40

Val Asp Phe Ser Leu Gly Glu Trp Lys Thr Gln Met Glu Glu Thr Lys
         45              50              55

Ala Gln Asp Ile Leu Gly Ala Val Thr Leu Leu Glu Gly Val Met
 60              65              70                      75

Ala Ala Arg Gly Gln Leu Gly Pro Thr Cys Leu Ser Ser Leu Leu Gly
                 80              85              90

Gln Leu Ser Gly Gln Val Arg Leu Leu Leu Gly Ala Leu Gln Ser Leu
             95              100             105

Leu Gly Thr Gln Leu Pro Pro Gln Gly Arg Thr Thr Ala His Lys Asp
         110             115             120

Pro Asn Ala Ile Phe Leu Ser Phe Gln His Leu Leu Arg Gly Lys Val
         125             130             135

Arg Phe Leu Met Leu Val Gly Ser Thr Leu Cys Val Arg Gly Gly
140             145             150                     155

Gly Ser Gly Gly Gly Ser Gly Gly Gly Ser Arg Ala Pro Thr Tyr Arg
             160             165             170

Ala Ser Ser Leu Pro Gln Ser Phe Leu Leu Lys Ser Leu Glu Gln Val
             175             180             185

Arg Lys Ile Gln Gly Asp Gly Ala Ala Leu Gln Glu Lys Leu Cys Ala
             190             195             200

Thr Tyr Lys Leu Cys His Pro Glu Glu Leu Val Leu Leu Gly His Ser
         205             210             215

Leu Gly Ile Pro Trp Ala Pro Leu Ser Ser Cys Pro Ser Gln Ala Leu
220             225             230             235

Gln Leu Ala Gly Cys Leu Ser Gln Leu His Ser Gly Leu Phe Leu Tyr
                 240             245             250

Gln Gly Leu Leu Gln Ala Leu Glu Gly Ile Ser Pro Glu Leu Gly Pro
             255             260             265

Thr Leu Asp Thr Leu Gln Leu Asp Val Ala Asp Phe Ala Thr Thr Ile
         270             275             280

Trp Gln Gln Met Glu Glu Leu Gly Met Ala Pro Ala Leu Gln Pro Thr
285             290             295

Gln Gly Ala Met Pro Ala Phe Ala Ser Ala Phe Gln Arg Arg Ala Gly
300             305             310             315

Gly Val Leu Val Ala Ser His Leu Gln Ser Phe Leu Glu Val Ser Tyr
                 320             325             330

Arg Val Leu Arg His Leu Ala Gln Pro
             335             340

(2) INFORMATION FOR SEQ ID NO: 8:

(i) SEQUENCE CHARACTERISTICS:
        (A) LENGTH: 1095 base pairs
        (B) TYPE: nucleic acid
        (C) STRANDEDNESS: double
        (D) TOPOLOGY: linear
```

-continued (ii) MOLECULE TYPE: other nucleic acid
    (A) DESCRIPTION: /desc = "synthetic DNA"

(ix) FEATURE:
    (A) NAME/KEY: mat_peptide
    (B) LOCATION: 64..1095

(ix) FEATURE:
    (A) NAME/KEY: CDS
    (B) LOCATION: 1..1095

(xi) SEQUENCE DESCRIPTION: SEQ ID NO: 8:

```
ATG GAG CTG ACT GAA TTG CTC CTC GTG GTC ATG CTT CTC CTA ACT GCA        48
Met Glu Leu Thr Glu Leu Leu Leu Val Val Met Leu Leu Leu Thr Ala
-21 -20              -15                  -10

AGG CTA ACG CTG TCC AGC CCG GCT CCT CCT GCT TGT GAC CTC CGA GTC        96
Arg Leu Thr Leu Ser Ser Pro Ala Pro Pro Ala Cys Asp Leu Arg Val
 -5                   1               5                  10

CTC AGT AAA CTG CTT CGT GAC TCC CAT GTC CTT CAC AGC AGA CTG AGC       144
Leu Ser Lys Leu Leu Arg Asp Ser His Val Leu His Ser Arg Leu Ser
                 15                  20                  25

CAG TGC CCA GAG GTT CAC CCT TTG CCT ACA CCT GTC CTG CTG CCT GCT       192
Gln Cys Pro Glu Val His Pro Leu Pro Thr Pro Val Leu Leu Pro Ala
             30                  35                  40

GTG GAC TTT AGC TTG GGA GAA TGG AAA ACC CAG ATG GAG GAG ACC AAG       240
Val Asp Phe Ser Leu Gly Glu Trp Lys Thr Gln Met Glu Glu Thr Lys
         45                  50                  55

GCA CAG GAC ATT CTG GGA GCA GTG ACC CTT CTG CTG GAG GGA GTG ATG       288
Ala Gln Asp Ile Leu Gly Ala Val Thr Leu Leu Leu Glu Gly Val Met
 60              65                  70                  75

GCA GCA CGG GGA CAA CTG GGA CCC ACT TGC CTC TCA TCC CTC CTG GGG       336
Ala Ala Arg Gly Gln Leu Gly Pro Thr Cys Leu Ser Ser Leu Leu Gly
                 80                  85                  90

CAG CTT TCT GGA CAG GTC CGT CTC CTC CTT GGG GCC CTG CAG AGC CTC       384
Gln Leu Ser Gly Gln Val Arg Leu Leu Leu Gly Ala Leu Gln Ser Leu
             95                 100                 105

CTT GGA ACC CAG CTT CCT CCA CAG GGC AGG ACC ACA GCT CAC AAG GAT       432
Leu Gly Thr Gln Leu Pro Pro Gln Gly Arg Thr Thr Ala His Lys Asp
         110                 115                 120

CCC AAT GCC ATC TTC CTG AGC TTC CAA CAC CTG CTC CGA GGA AAG GTG       480
Pro Asn Ala Ile Phe Leu Ser Phe Gln His Leu Leu Arg Gly Lys Val
125                 130                 135

CGT TTC CTG ATG CTT GTA GGA GGG TCC ACC CTC TGC GTA CGG TCC GGA       528
Arg Phe Leu Met Leu Val Gly Gly Ser Thr Leu Cys Val Arg Ser Gly
140                 145                 150                 155

GGT GGC TCT GGC GGT GGT TCT GGT GGC GGC TCC GGA GGC GGT CGT GCG       576
Gly Gly Ser Gly Gly Gly Ser Gly Gly Gly Ser Gly Gly Gly Arg Ala
             160                 165                 170

CCA ACA TAT CGC GCC TCG AGT CTA CCA CAG AGC TTC CTT TTA AAA AGC       624
Pro Thr Tyr Arg Ala Ser Ser Leu Pro Gln Ser Phe Leu Leu Lys Ser
         175                 180                 185

TTA GAG CAA GTG AGG AAG ATC CAG GGC GAT GGC GCA GCG CTC CAG GAG       672
Leu Glu Gln Val Arg Lys Ile Gln Gly Asp Gly Ala Ala Leu Gln Glu
         190                 195                 200

AAG CTG TGT GCC ACC TAC AAG CTG TGC CAC CCC GAG GAG CTG GTG CTG       720
Lys Leu Cys Ala Thr Tyr Lys Leu Cys His Pro Glu Glu Leu Val Leu
205                 210                 215

CTC GGA CAC TCT CTG GGC ATC CCC TGG GCT CCC CTG AGC AGC TGC CCC       768
Leu Gly His Ser Leu Gly Ile Pro Trp Ala Pro Leu Ser Ser Cys Pro
220                 225                 230                 235

AGC CAG GCC CTG CAG CTG GCA GGC TGC TTG AGC CAA CTC CAT AGC GGC       816
Ser Gln Ala Leu Gln Leu Ala Gly Cys Leu Ser Gln Leu His Ser Gly
```

-continued

```
                 240                 245                 250
CTT TTC CTC TAC CAG GGG CTC CTG CAG GCC CTG GAA GGG ATC TCC CCC    864
Leu Phe Leu Tyr Gln Gly Leu Leu Gln Ala Leu Glu Gly Ile Ser Pro
            255                 260                 265

GAG TTG GGT CCC ACC TTG GAC ACA CTG CAG CTG GAC GTC GCC GAC TTT    912
Glu Leu Gly Pro Thr Leu Asp Thr Leu Gln Leu Asp Val Ala Asp Phe
        270                 275                 280

GCC ACC ACC ATC TGG CAG CAG ATG GAA GAA CTG GGA ATG GCC CCT GCC    960
Ala Thr Thr Ile Trp Gln Gln Met Glu Glu Leu Gly Met Ala Pro Ala
    285                 290                 295

CTG CAG CCC ACC CAG GGT GCC ATG CCG GCC TTC GCC TCT GCT TTC CAG   1008
Leu Gln Pro Thr Gln Gly Ala Met Pro Ala Phe Ala Ser Ala Phe Gln
300                 305                 310                 315

CGC CGG GCA GGA GGG GTC CTA GTT GCC TCC CAT CTG CAG AGC TTC CTG   1056
Arg Arg Ala Gly Gly Val Leu Val Ala Ser His Leu Gln Ser Phe Leu
                320                 325                 330

GAG GTG TCG TAC CGC GTT CTA CGC CAC CTT GCC CAG CCC                1095
Glu Val Ser Tyr Arg Val Leu Arg His Leu Ala Gln Pro
            335                 340
```

(2) INFORMATION FOR SEQ ID NO: 9:

(i) SEQUENCE CHARACTERISTICS:
        (A) LENGTH: 365 amino acids
        (B) TYPE: amino acid
        (D) TOPOLOGY: linear (ii) MOLECULE TYPE: protein (xi) SEQUENCE DESCRIPTION: SEQ ID NO: 9:

```
Met Glu Leu Thr Glu Leu Leu Leu Val Val Met Leu Leu Thr Ala
-21 -20                 -15                 -10

Arg Leu Thr Leu Ser Ser Pro Ala Pro Pro Ala Cys Asp Leu Arg Val
-5                   1                   5                  10

Leu Ser Lys Leu Leu Arg Asp Ser His Val Leu His Ser Arg Leu Ser
            15                  20                  25

Gln Cys Pro Glu Val His Pro Leu Pro Thr Pro Val Leu Leu Pro Ala
        30                  35                  40

Val Asp Phe Ser Leu Gly Glu Trp Lys Thr Gln Met Glu Glu Thr Lys
    45                  50                  55

Ala Gln Asp Ile Leu Gly Ala Val Thr Leu Leu Leu Glu Gly Val Met
60                  65                  70                  75

Ala Ala Arg Gly Gln Leu Gly Pro Thr Cys Leu Ser Ser Leu Leu Gly
            80                  85                  90

Gln Leu Ser Gly Gln Val Arg Leu Leu Leu Gly Ala Leu Gln Ser Leu
        95                 100                 105

Leu Gly Thr Gln Leu Pro Pro Gln Gly Arg Thr Thr Ala His Lys Asp
    110                 115                 120

Pro Asn Ala Ile Phe Leu Ser Phe Gln His Leu Leu Arg Gly Lys Val
125                 130                 135

Arg Phe Leu Met Leu Val Gly Gly Ser Thr Leu Cys Val Arg Ser Gly
140                 145                 150                 155

Gly Gly Ser Gly Gly Gly Ser Gly Gly Gly Ser Gly Gly Gly Arg Ala
            160                 165                 170

Pro Thr Tyr Arg Ala Ser Ser Leu Pro Gln Ser Phe Leu Leu Lys Ser
        175                 180                 185

Leu Glu Gln Val Arg Lys Ile Gln Gly Asp Gly Ala Ala Leu Gln Glu
    190                 195                 200
```

```
Lys Leu Cys Ala Thr Tyr Lys Leu Cys His Pro Glu Glu Leu Val Leu
    205                 210                 215

Leu Gly His Ser Leu Gly Ile Pro Trp Ala Pro Leu Ser Ser Cys Pro
220                 225                 230                 235

Ser Gln Ala Leu Gln Leu Ala Gly Cys Leu Ser Gln Leu His Ser Gly
                240                 245                 250

Leu Phe Leu Tyr Gln Gly Leu Leu Gln Ala Leu Glu Gly Ile Ser Pro
                255                 260                 265

Glu Leu Gly Pro Thr Leu Asp Thr Leu Gln Leu Asp Val Ala Asp Phe
            270                 275                 280

Ala Thr Thr Ile Trp Gln Gln Met Glu Glu Leu Gly Met Ala Pro Ala
        285                 290                 295

Leu Gln Pro Thr Gln Gly Ala Met Pro Ala Phe Ala Ser Ala Phe Gln
300                 305                 310                 315

Arg Arg Ala Gly Gly Val Leu Val Ala Ser His Leu Gln Ser Phe Leu
                320                 325                 330

Glu Val Ser Tyr Arg Val Leu Arg His Leu Ala Gln Pro
            335                 340
```

(2) INFORMATION FOR SEQ ID NO: 10:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: sig_peptide
        (B) LOCATION: 27..44

(xi) SEQUENCE DESCRIPTION: SEQ ID NO: 10:

CTCTCCAAGC TTGAATTCCG GCCAGAATGG AGCTGACTGA ATTG          44

(2) INFORMATION FOR SEQ ID NO: 11:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 11:

GTAGAGGTAC CGCGGCCGCT TACCCTTCCT GAGACAGATT CTGGGAG       47

(2) INFORMATION FOR SEQ ID NO: 12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 12:

TGAACCTCTG GGCACTGGCT CAGT          24

(2) INFORMATION FOR SEQ ID NO: 13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 13:

GCTGCCTGCT GTGGACTTTA GCTT                                            24

(2) INFORMATION FOR SEQ ID NO: 14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: CDS
        (B) LOCATION: 1..24

(xi) SEQUENCE DESCRIPTION: SEQ ID NO: 14:

TGT TGG AAG CTC AGG AAG ATG GCA                                       24
Cys Trp Lys Leu Arg Lys Met Ala
 1               5

(2) INFORMATION FOR SEQ ID NO: 15:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO: 15:

Cys Trp Lys Leu Arg Lys Met Ala
 1               5

(2) INFORMATION FOR SEQ ID NO: 16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: CDS
        (B) LOCATION: 1..24

(xi) SEQUENCE DESCRIPTION: SEQ ID NO: 16:

CCT GAT GCT TGT AGG AGG GTC CAC                                       24
Pro Asp Ala Cys Arg Arg Val His
 1               5

(2) INFORMATION FOR SEQ ID NO: 17:

```
    (i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO: 17:

Pro Asp Ala Cys Arg Arg Val His
 1               5

(2) INFORMATION FOR SEQ ID NO: 18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: CDS
        (B) LOCATION: 1..24

(xi) SEQUENCE DESCRIPTION: SEQ ID NO: 18:

TCA AGA GTT CGT GTA TCC TGT TCA                            24
Ser Arg Val Arg Val Ser Cys Ser
 1               5

(2) INFORMATION FOR SEQ ID NO: 19:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO: 19:

Ser Arg Val Arg Val Ser Cys Ser
 1               5

(2) INFORMATION FOR SEQ ID NO: 20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: CDS
        (B) LOCATION: 1..24

(xi) SEQUENCE DESCRIPTION: SEQ ID NO: 20:

GAA TGG AAC TCG TGG ACT CTT TCC                            24
Glu Trp Asn Ser Trp Thr Leu Ser
 1               5

(2) INFORMATION FOR SEQ ID NO: 21:

(i) SEQUENCE CHARACTERISTICS:
        (A) LENGTH: 8 amino acids
        (B) TYPE: amino acid
        (D) TOPOLOGY: linear
```

(ii) MOLECULE TYPE: protein (xi) SEQUENCE DESCRIPTION: SEQ ID NO: 21:

Glu Trp Asn Ser Trp Thr Leu Ser
 1               5

(2) INFORMATION FOR SEQ ID NO: 22:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO: 22:

GTAAAACGAC GGCCAGT                                                      17

(2) INFORMATION FOR SEQ ID NO: 23:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO: 23:

CAGGAAACAG CTATGAC                                                      17

(2) INFORMATION FOR SEQ ID NO: 24:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 24:

Gly Gly Gly Ser Gly Gly Gly Ser Gly Gly Gly Ser Arg
 1               5                  10

(2) INFORMATION FOR SEQ ID NO: 25:

(i) SEQUENCE CHARACTERISTICS:
            (A) LENGTH: 66 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(ix) FEATURE:
            (A) NAME/KEY: CDS
            (B) LOCATION: join(1..3, 43..66)

(xi) SEQUENCE DESCRIPTION: SEQ ID NO: 25:

TGC TCTAGAACCG CCTCCGGAAC CACCTCCAGA ACCGCCACC CCT GAC GCA GAG          54
Cys                                             Pro Asp Ala Glu
 1                                                           5
GGT GGA CCC TCC                                                         66
Gly Gly Pro Ser (2) INFORMATION FOR SEQ ID NO: 26:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO: 26:

Cys Pro Asp Ala Glu Gly Gly Pro Ser
 1               5

(2) INFORMATION FOR SEQ ID NO: 27:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: CDS
        (B) LOCATION: 22..45

(xi) SEQUENCE DESCRIPTION: SEQ ID NO: 27:

GGTTCCGGAG GCGGTTCTAG A GCA CCA ACA TAT CGC GCC TCG AGT         45
                        Ala Pro Thr Tyr Arg Ala Ser Ser
                         1               5

(2) INFORMATION FOR SEQ ID NO: 28:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO: 28:

Ala Pro Thr Tyr Arg Ala Ser Ser
 1               5

(2) INFORMATION FOR SEQ ID NO: 29:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 29:

CATTCCGCGG GGTACCGCGG CCGCTCAGGG CTGGGCAAGG TGGCGTAG           48

(2) INFORMATION FOR SEQ ID NO: 30:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid

```
        (A) DESCRIPTION: /desc = "synthetic DNA"

(ix) FEATURE:
        (A) NAME/KEY: CDS
        (B) LOCATION: 1..24

(xi) SEQUENCE DESCRIPTION: SEQ ID NO: 30:

GGC TGC TTG AGC CAA CTC CAT AGC                                     24
Gly Cys Leu Ser Gln Leu His Ser
 1               5

(2) INFORMATION FOR SEQ ID NO: 31:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO: 31:

Gly Cys Leu Ser Gln Leu His Ser
 1               5

(2) INFORMATION FOR SEQ ID NO: 32:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: CDS
        (B) LOCATION: 1..24

(xi) SEQUENCE DESCRIPTION: SEQ ID NO: 32:

GAC CCA ACT CGG GGG AGA TCC CTT                                     24
Asp Pro Thr Arg Gly Arg Ser Leu
 1               5

(2) INFORMATION FOR SEQ ID NO: 33:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO: 33:

Asp Pro Thr Arg Gly Arg Ser Leu
 1               5

(2) INFORMATION FOR SEQ ID NO: 34:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: mutation
        (B) LOCATION: replace(25, "")
```

(ix) FEATURE:
        (A) NAME/KEY: mutation
        (B) LOCATION: replace(33..34, "")

(xi) SEQUENCE DESCRIPTION: SEQ ID NO: 34:

TAGACTCGAG GCGCGATATG TTGGCGCCCG CCGTACGCAG AGGGTGGACC CTCCTAC        57

(2) INFORMATION FOR SEQ ID NO: 35:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 35:

Ser Gly Gly Gly Ser Gly Gly Gly Ser Gly Gly Gly Ser Gly Gly Gly
1               5                   10                  15
Arg (2) INFORMATION FOR SEQ ID NO: 36:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: CDS
        (B) LOCATION: 1..6

(ix) FEATURE:
        (A) NAME/KEY: misc_feature
        (B) LOCATION: 7..57
        (D) OTHER INFORMATION: /product= "linker peptide"

(ix) FEATURE:
        (A) NAME/KEY: misc_feature
        (B) LOCATION: 1..5
        (D) OTHER INFORMATION: /product= "SplI"

(ix) FEATURE:
        (A) NAME/KEY: misc_feature
        (B) LOCATION: 7..12
        (D) OTHER INFORMATION: /product= "MroI"

(ix) FEATURE:
        (A) NAME/KEY: misc_feature
        (B) LOCATION: 43..48
        (D) OTHER INFORMATION: /product= "MroI"

(ix) FEATURE:
        (A) NAME/KEY: misc_feature
        (B) LOCATION: 58..61
        (D) OTHER INFORMATION: /product= "BbeI"

(ix) FEATURE:
        (A) NAME/KEY: mutation
        (B) LOCATION: replace(4..5, "")

(xi) SEQUENCE DESCRIPTION: SEQ ID NO: 36:

GTA CGG TCCGGAGGTG GCTCTGGCGG TGGTTCTGGT GGCGGCTCCG GAGGCGGTCG        56
Val Arg
 1
TGCGC                                                                 61

(2) INFORMATION FOR SEQ ID NO: 37:

(i) SEQUENCE CHARACTERISTICS:
        (A) LENGTH: 2 amino acids
        (B) TYPE: amino acid
        (D) TOPOLOGY: linear (ii) MOLECULE TYPE: protein (xi) SEQUENCE DESCRIPTION: SEQ ID NO: 37:

Val Arg
 1

(2) INFORMATION FOR SEQ ID NO: 38:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: misc_feature
        (B) LOCATION: 1..51
        (D) OTHER INFORMATION: /product= "linker peptide"

(ix) FEATURE:
        (A) NAME/KEY: misc_feature
        (B) LOCATION: 53
        (D) OTHER INFORMATION: /product= "SplI"

(ix) FEATURE:
        (A) NAME/KEY: misc_feature
        (B) LOCATION: 10..15
        (D) OTHER INFORMATION: /product= "MroI"

(ix) FEATURE:
        (A) NAME/KEY: misc_feature
        (B) LOCATION: 46..51
        (D) OTHER INFORMATION: /product= "MroI"

(xi) SEQUENCE DESCRIPTION: SEQ ID NO: 38:

ACGACCGCCT CCGGAGCCGC CACCAGAACC ACCGCCAGAG CCACCTCCGG ACC            53

(2) INFORMATION FOR SEQ ID NO: 39:

(i) SEQUENCE CHARACTERISTICS:
        (A) LENGTH: 175 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: misc_feature
        (B) LOCATION: 1
        (D) OTHER INFORMATION: Xaa = Met (xi) SEQUENCE DESCRIPTION: SEQ ID NO: 39:

Xaa Thr Pro Leu Gly Pro Ala Ser Ser Leu Pro Gln Ser Phe Leu Leu
 1               5                  10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Gly Leu
        35                  40                  45

-continued

```
Val Leu Leu Gly His Ser Leu Gly Ile Pro Trp Ala Pro Leu Ser Ser
 50                  55                  60
Cys Pro Ser Gln Ala Leu Gln Leu Ala Gly Cys Leu Ser Gln Leu His
 65                  70                  75                  80
Ser Gly Leu Phe Leu Tyr Gln Gly Leu Leu Gln Ala Leu Glu Gly Ile
                 85                  90                  95
Ser Pro Glu Leu Gly Pro Thr Leu Asp Thr Leu Gln Leu Asp Val Ala
                100                 105                 110
Asp Phe Ala Thr Thr Ile Trp Gln Gln Met Glu Glu Leu Gly Met Ala
                115                 120                 125
Pro Ala Leu Gln Pro Thr Gln Gly Ala Met Pro Ala Phe Ala Ser Ala
130                 135                 140
Phe Gln Arg Arg Ala Gly Gly Val Leu Val Ala Ser His Leu Gln Ser
145                 150                 155                 160
Phe Leu Glu Val Ser Tyr Arg Val Leu Arg His Leu Ala Gln Pro
                165                 170                 175
```

(2) INFORMATION FOR SEQ ID NO: 40:

(i) SEQUENCE CHARACTERISTICS:
  (A) LENGTH: 332 amino acids
  (B) TYPE: amino acid
  (C) STRANDEDNESS: <Unknown>
  (D) TOPOLOGY: linear (ii) MOLECULE TYPE: peptide (xi) SEQUENCE DESCRIPTION: SEQ ID NO: 40:

```
Ser Pro Ala Pro Pro Ala Cys Asp Leu Arg Val Leu Ser Lys Leu Leu
 1               5                  10                  15
Arg Asp Ser His Val Leu His Ser Arg Leu Ser Gln Cys Pro Glu Val
                 20                  25                  30
His Pro Leu Pro Thr Pro Val Leu Leu Pro Ala Val Asp Phe Ser Leu
                 35                  40                  45
Gly Glu Trp Lys Thr Gln Met Glu Glu Thr Lys Ala Gln Asp Ile Leu
 50                  55                  60
Gly Ala Val Thr Leu Leu Leu Glu Gly Val Met Ala Ala Arg Gly Gln
 65                  70                  75                  80
Leu Gly Pro Thr Cys Leu Ser Ser Leu Leu Gly Gln Leu Ser Gly Gln
                 85                  90                  95
Val Arg Leu Leu Leu Gly Ala Leu Gln Ser Leu Leu Gly Thr Gln Leu
                100                 105                 110
Pro Pro Gln Gly Arg Thr Thr Ala His Lys Asp Pro Asn Ala Ile Phe
                115                 120                 125
Leu Ser Phe Gln His Leu Leu Arg Gly Lys Val Arg Phe Leu Met Leu
130                 135                 140
Val Gly Gly Ser Thr Leu Cys Val Arg Arg Ala Pro Pro Thr Thr Ala
145                 150                 155                 160
Val Pro Ser Arg Thr Ser Leu Val Leu Thr Leu Asn Glu Leu Pro Asn
                165                 170                 175
Arg Thr Ser Gly Leu Leu Glu Thr Asn Phe Thr Ala Ser Ala Arg Thr
                180                 185                 190
Thr Gly Ser Gly Leu Leu Lys Trp Gln Gln Gly Phe Arg Ala Lys Ile
                195                 200                 205
Pro Gly Leu Leu Asn Gln Thr Ser Arg Ser Leu Asp Gln Ile Pro Gly
210                 215                 220
```

```
Tyr Leu Asn Arg Ile His Glu Leu Leu Asn Gly Thr Arg Gly Leu Phe
225                 230                 235                 240

Pro Gly Pro Ser Arg Arg Thr Leu Gly Ala Pro Asp Ile Ser Ser Gly
            245                 250                 255

Thr Ser Asp Thr Gly Ser Leu Pro Pro Asn Leu Gln Pro Gly Tyr Ser
            260                 265                 270

Pro Ser Pro Thr His Pro Pro Thr Gly Gln Tyr Thr Leu Phe Pro Leu
        275                 280                 285

Pro Pro Thr Leu Pro Thr Pro Val Val Gln Leu His Pro Leu Leu Pro
        290                 295                 300

Asp Pro Ser Ala Pro Thr Pro Thr Pro Thr Ser Pro Leu Leu Asn Thr
305                 310                 315                 320

Ser Tyr Thr His Ser Gln Asn Leu Ser Gln Glu Gly
                325                 330
```

(2) INFORMATION FOR SEQ ID NO: 41:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 41:

```
Ser Gly Gly Gly Arg
1               5
```

(2) INFORMATION FOR SEQ ID NO: 42:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 42:

```
Ser Gly Gly Gly Ser Gly Gly Gly Ser Gly Gly Gly Ser Gly Gly Gly
1               5                   10                  15
```

(2) INFORMATION FOR SEQ ID NO: 43:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 43:

```
Ser Gly Gly Gly
1
```

(2) INFORMATION FOR SEQ ID NO: 44:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide -continued (xi) SEQUENCE DESCRIPTION: SEQ ID NO: 44:

Gly Gly Gly Ser Gly Gly Gly Ser Gly Gly Gly Ser
1               5                   10

(2) INFORMATION FOR SEQ ID NO: 45:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 45:

Gly Gly Gly Ser Gly Gly Gly Ser
1               5

(2) INFORMATION FOR SEQ ID NO: 46:

(i) SEQUENCE CHARACTERISTICS:
        (A) LENGTH: 174 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 46:

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Gly Leu Val
            35                  40                  45

Leu Leu Gly His Ser Leu Gly Ile Pro Trp Ala Pro Leu Ser Ser Cys
        50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
            130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170